(12) United States Patent
Yoshino

(10) Patent No.: US 9,474,443 B2
(45) Date of Patent: Oct. 25, 2016

(54) OPHTHALMIC APPARATUS

(71) Applicant: NIDEK CO., LTD., Gamagori-shi, Aichi (JP)

(72) Inventor: Masayuki Yoshino, Obu (JP)

(73) Assignee: NIDEK CO., LTD., Gamagori-shi (JP)

( * ) Notice: Subject to any disclaimer, the term of this patent is extended or adjusted under 35 U.S.C. 154(b) by 0 days.

(21) Appl. No.: 14/734,107

(22) Filed: Jun. 9, 2015

(65) Prior Publication Data

US 2015/0374232 A1     Dec. 31, 2015

(30) Foreign Application Priority Data

Jun. 25, 2014 (JP) .................. 2014-130461

(51) Int. Cl.
*A61B 3/12* (2006.01)
*A61B 3/14* (2006.01)

(52) U.S. Cl.
CPC .. *A61B 3/12* (2013.01); *A61B 3/14* (2013.01)

(58) Field of Classification Search
CPC ........... A61B 3/12; A61B 3/14; A61B 3/102
USPC ................. 351/206, 221, 246, 205
See application file for complete search history.

(56) References Cited

U.S. PATENT DOCUMENTS

2015/0116660 A1*  4/2015 Matsumoto ............ A61B 3/102
                                                                    351/206

FOREIGN PATENT DOCUMENTS

JP      H06-51024 B2     7/1994
JP      2009-066109 A    4/2009

* cited by examiner

*Primary Examiner* — Hung Dang
(74) *Attorney, Agent, or Firm* — Oliff PLC

(57) ABSTRACT

An ophthalmic apparatus includes: an imaging optical system including an imaging diaphragm placed between an objective lens and an imaging device to restrict light from a fundus, the light having passed through a position conjugate with an examinee's pupil, to image a fundus image by the imaging device through the objective lens and the imaging diaphragm; a first light projecting optical system to project light having a first wavelength emitted from a first light source and restricted in range for passage through the pupil, as autofluorescence-inducing excitation light to the eye through the objective lens; and a first optical-path combining member to allow the imaging optical system and the first light projecting optical system to share at least part of an optical path. The first optical-path combining member is provided between the objective lens and a conjugate position with the pupil through the objective lens in the imaging optical system.

10 Claims, 6 Drawing Sheets

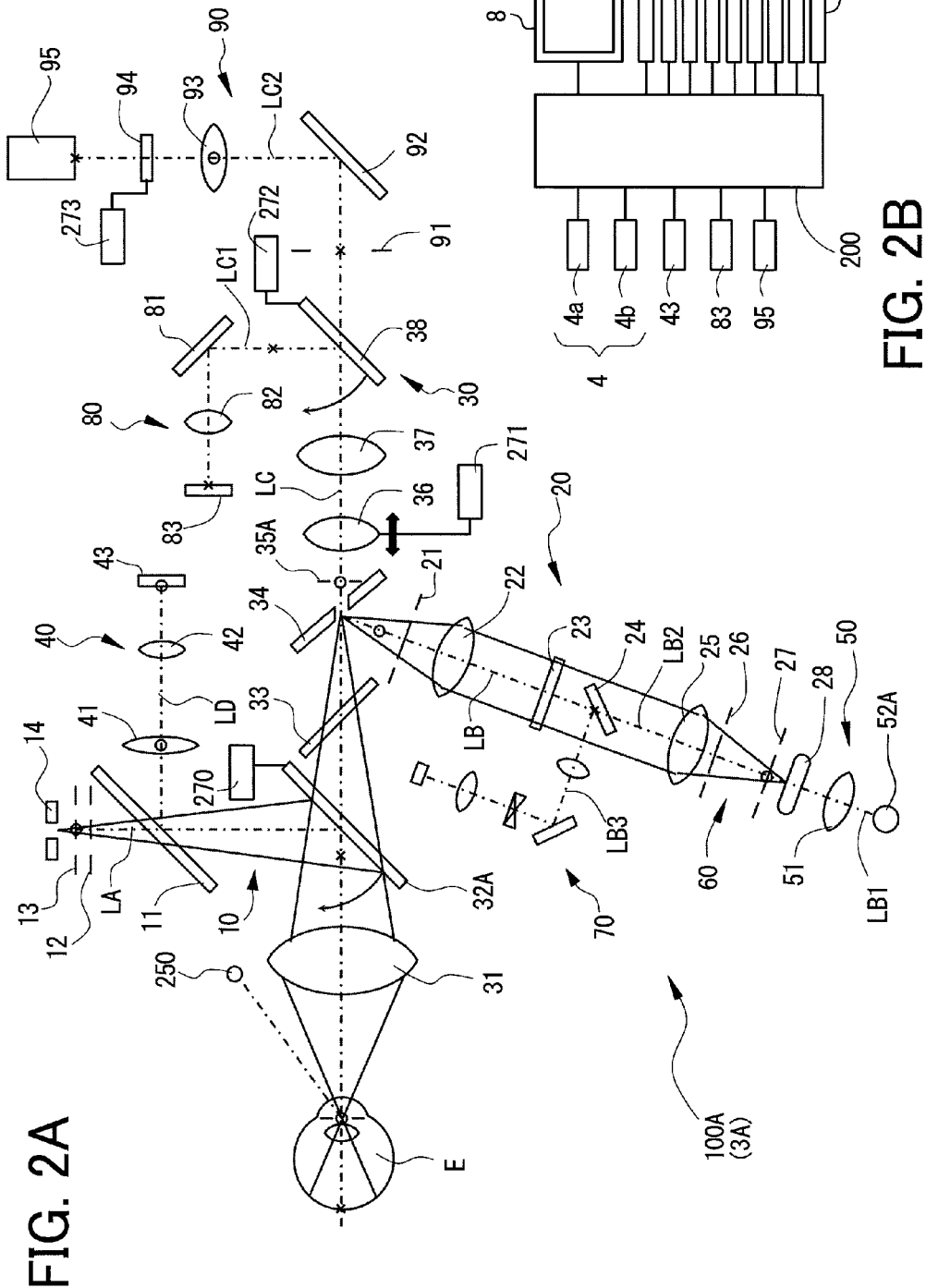

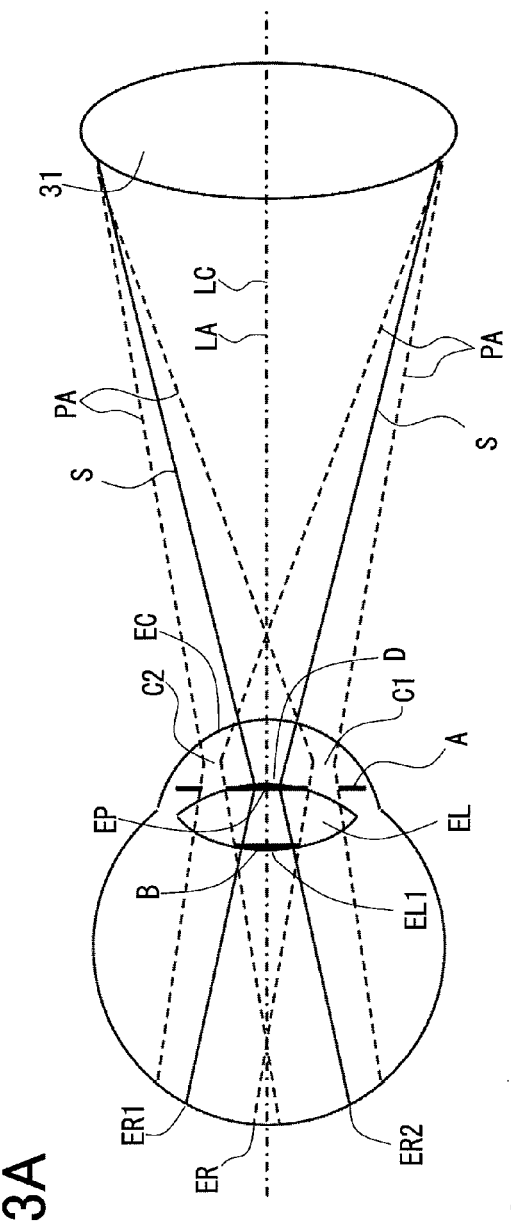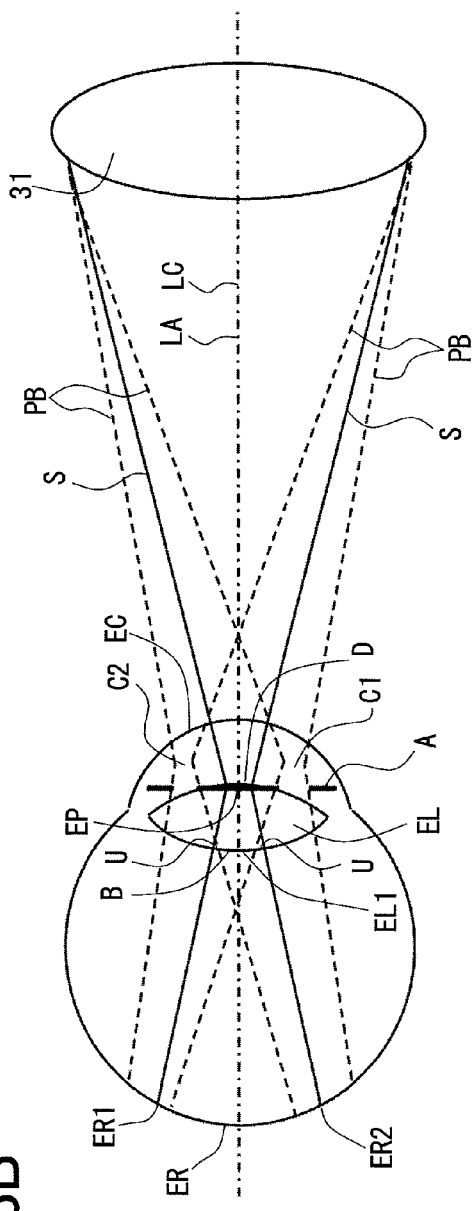
FIG. 3A
FIG. 3B

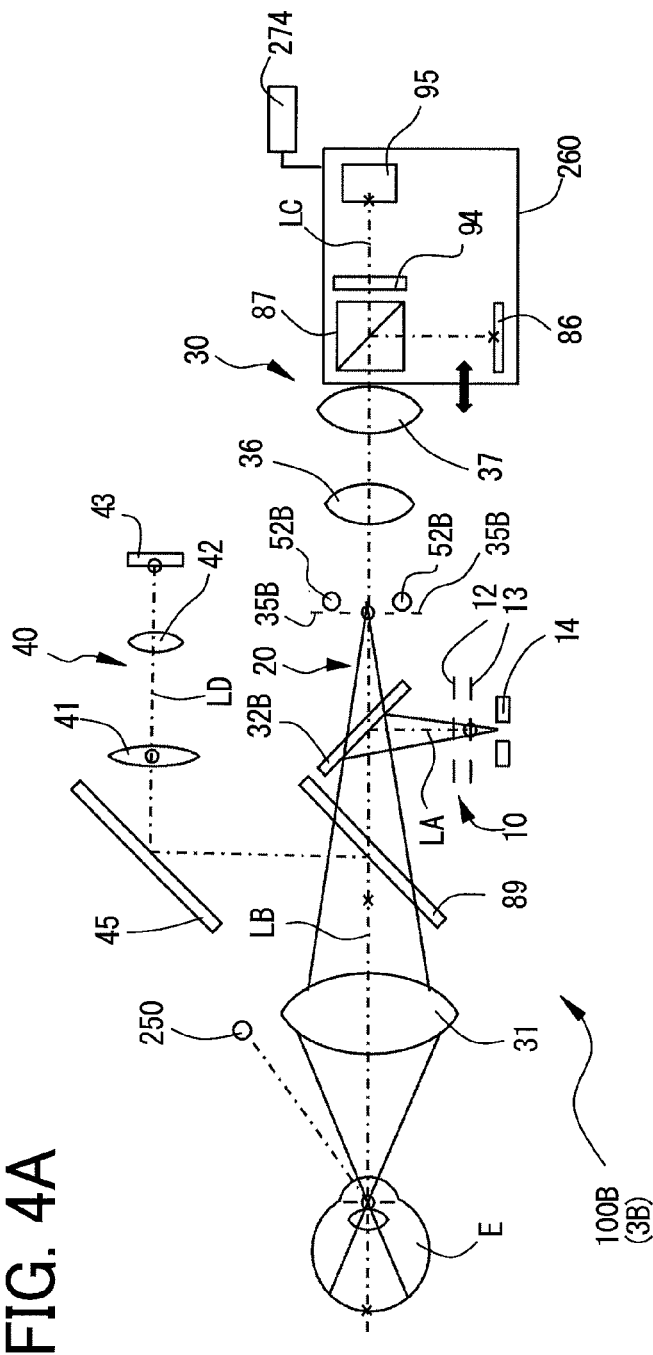
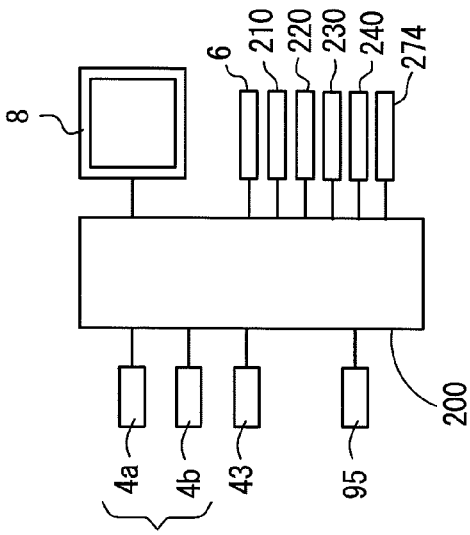
FIG. 4A
FIG. 4B

OPHTHALMIC APPARATUS

CROSS-REFERENCE TO RELATED APPLICATIONS

This application is based upon and claims the benefit of priority from the prior Japanese Patent Application No. 2014-130461 filed on Jun. 25, 2014, the entire contents of which are incorporated herein by reference.

BACKGROUND

This disclosure relates to an ophthalmic apparatus for obtaining fundus information of an examinee's eye.

As the ophthalmic apparatus for obtaining fundus information of an examinee's eye, there is known an ophthalmic apparatus arranged to rotate a turret provided in an illumination optical system, thereby narrowing a bandwidth of light emitted from a photographing light source to generate excitation light, to obtain a fluorescence fundus image from fluorescence occurring in the fundus illuminated with excitation light (see Japanese patent unexamined application publication No. 2009-66109). This apparatus of JP-A-2009-66109 is configured such that a perforated mirror is placed as an optical path splitting or branching member at a position that is firstly conjugated with a pupil of the examiner's eye through an objective lens, and a light shielding plate having a ring-shaped opening at a position conjugated with the pupil (a position that is secondly conjugated with the pupil through the objective lens) on an optical path split or branched by the optical path splitting member.

Regarding a fundus photographing apparatus, called a fundus camera, irrespective of installation of a fluorescence photographing function, there is widely used a technique of placing a plurality of light shielding members each having a ring-shaped opening in different positions to reduce unnecessary or unwanted reflection light arising in a portion other than a fundus of an examinee's eye by illumination light (see Japanese patent examined publication No. H6-51024(1994), for example).

SUMMARY

However, when the light shielding members are placed in the illumination optical system, fundus information with reduced unwanted reflection light is obtained, whereas, the light emitted from the light source is apt to be reduced by the light shielding members. To obtain fluorescence of a fundus of an examinee's eye, a large light amount is required in normal color photographing and others. In particular, autofluorescence photographing for capturing or imaging the fluorescence reaction in a fundus of an examinee's eye without injecting (injection) a fluorescent agent into the eye needs a larger light emission amount than that in normal fluorescence photographing called FAG To increase the light emission amount of a light source, irrespective of color photographing and fluorescence photographing, it is necessary to provide a complicated or expensive light source.

The present disclosure has a purpose to provide an ophthalmic apparatus capable of obtaining appropriate fundus image by use of an optical system suitable for fluorescence photographing even by a simple structure.

To achieve the above purpose, one aspect of the present disclosure provides an ophthalmic apparatus including: an imaging optical system including an imaging diaphragm placed between an objective lens and an imaging device to restrict light from a fundus, the light having passed through a position conjugate with a pupil of an examinee's eye, the imaging optical system being configured to image a fundus image of the examinee's eye by use of the imaging device through the objective lens and the imaging diaphragm; a first light projecting optical system including a first light source to emit light having a first wavelength and being configured to project the light with the first wavelength, emitted from the first light source and restricted in range for passage through the pupil of the examinee's eye, as autofluorescence-inducing excitation light to the examinee's eye through the objective lens; and a first optical-path combining member configured to allow the imaging optical system and the first light projecting optical system to share at least part of an optical path with each other, wherein the first optical-path combining member is provided between the objective lens and a conjugate position to be conjugated with the pupil of the examinee's eye through the objective lens in the imaging optical system.

According to the present disclosure, an ophthalmic apparatus can be provided to be able to obtain an appropriate fundus image even by a simple structure.

BRIEF DESCRIPTION OF THE DRAWINGS

FIGS. 2A and 2B are explanatory views to explain optical systems and a control system of the ophthalmic apparatus shown in FIG. 1;

FIGS. 3A and 3B are conceptual diagrams of projection light beam and imaging light beam;

FIGS. 4A and 4B are explanatory views to explain optical systems and a control system of an ophthalmic apparatus of a second embodiment;

DETAILED DESCRIPTION OF THE EXEMPLARY EMBODIMENTS

A detailed description of typical embodiments of the present disclosure will now be given referring to the accompanying drawings.

1. First Embodiment

Firstly, an ophthalmic apparatus of the first embodiment according to the present disclosure will be explained referring to FIG. 1.

<1-1. Configuration>

Figure 1:
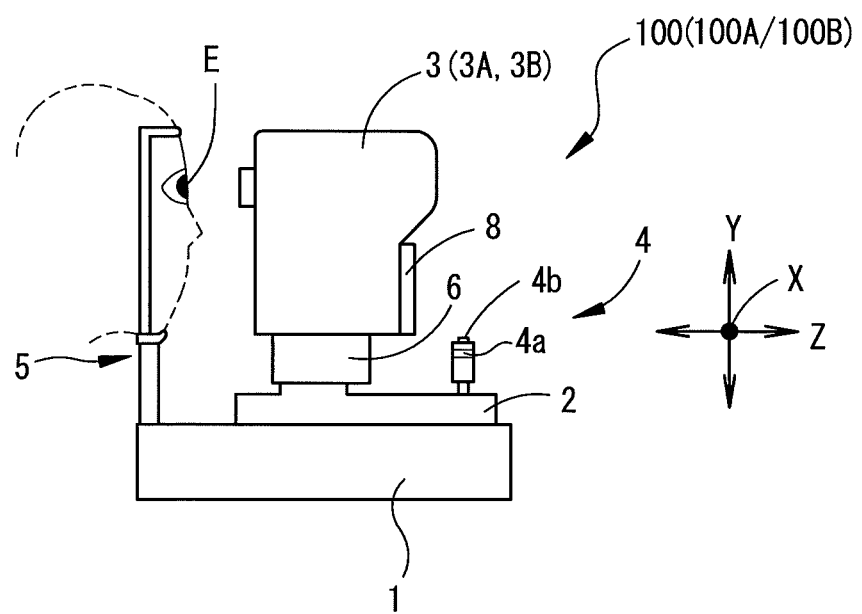
FIG. 1 is an external configuration view of an ophthalmic apparatus of a first embodiment.

FIG. 1 is an external configuration view of an ophthalmic apparatus 100A of the first embodiment. This ophthalmic apparatus 100A includes a base table 1, a movable unit 2, an imaging part 3 (3A), and a head support part 5. The ophthalmic apparatus 100A is an apparatus configured to obtain fundus information of an examinee's eye E. In the present embodiment, a fundus image of the examinee's eye E is obtained as the fundus information by use of the imaging part 3. The movable unit 2 is movable in a right and left direction (X direction) and a front and back (working distance) direction (Z direction) with respect to the base table 1. The imaging part 3 (an apparatus main unit) is provided to be movable in three dimensions with respect to the movable unit 2. The imaging part 3 accommodates various optical systems mentioned later. The head support part 5 is fixedly placed on the base table 1 to support the head of an examinee.

The ophthalmic apparatus 100A has an automatic movement mechanism and a manual movement mechanism. The automatic movement mechanism includes an electric motor. This automatic movement mechanism can relatively move the imaging part 3 with respect to the examinee's eye E. To be specific, the imaging part 3 includes an XYZ drive part (actuator) 6 that is provided in the movable unit 2. These XYZ drive part 6 and movable unit 2 are operative to move the imaging part 3 in the right and left direction (X direction), an up and down direction (Y direction), and the front and back direction (Z direction) with respect to the eye E. The manual movement mechanism includes an operating unit such as a joystick 4 (an operating member). In response to operation of the joystick 4, the imaging part 3 is moved relative to the eye E. More specifically, there is provided a sliding mechanism not shown for sliding the movable unit 2 on the base table 1. When the joystick 4 is operated, accordingly, the movable unit 2 is caused to slide on the base table 1 in the X- and Z-directions by the sliding mechanism. The joystick 4 has a rotary knob 4a and a photographing switch 4b. When an examiner rotates the rotary knob 4a, the XYZ drive part 6 is Y-driven to move the imaging part 3 in the up and down direction. When the examiner pushes the photographing switch 4b, a fundus image of a fundus ER of the examinee's eye E is obtained. The ophthalmic apparatus 100A has a monitor 8 serving as a display unit. The monitor 8 is placed on an examiner side of the imaging part 3. The monitor 8 displays thereon a fundus observation image, a fundus photographed image, an anterior segment observation image, and others. The movement mechanism is not limited to the above. For instance, the imaging part 3 may be moved with respect to the examinee's eye E by only the XYZ drive part 6.

FIGS. 2A and 2B are explanatory views to explain optical systems and a control system accommodated in the imaging part 3. In FIG. 2A, the imaging part 3 includes a first light projecting optical system 10, a second light projecting optical system 20, an imaging optical system 30, an anterior segment observation optical system 40, and a fixation target presenting optical system not shown. It is to be noted that the first light projecting optical system 10 has an optical axis LA, the second light projecting optical system 20 has an optical axis LB, the imaging optical system 30 has an optical axis LC, and the anterior segment observation optical system 40 has an optical axis LD. Each point denoted with a circular mark (o) on respective optical axes in FIG. 2A represents a position conjugate with a pupil EP of the eye E through an objective lens 31. Each point denoted with a cross mark (x) on respective optical axes in FIG. 2A represents a position conjugate with a fundus ER of the eye E through the objective lens 31. The meanings of the circular mark and the cross mark are the same as those in optical systems accommodated in an imaging part of an ophthalmic apparatus 100B of a second embodiment which will be mentioned later (see FIG. 4A). The term "conjugate" in the present disclosure does not necessarily mean a strict conjugate relationship. For instance, a conjugate relationship may be slightly displaced depending on the structure (e.g., a distance from a corneal vertex to a pupil surface, and a thickness of a crystalline lens) of the examinee's eye E. Therefore, the term "conjugate" in the present disclosure also includes such a slightly displaced conjugate relationship.

<1-2. Imaging Optical System>

The imaging optical system 30 of the present embodiment is an optical system for imaging a fundus of the examinee's eye E. This imaging optical system 30 includes a fundus observation optical system 80 and a fundus photographing optical system 90. The fundus observation optical system 80 of the present embodiment is an optical system for imaging the fundus ER of the eye E to which infrared light (substantially colorless light) is projected in order to observe the imaging optical system ER of the eye E. Projecting of the infrared light is to suppress a phenomenon that the pupil EP of the eye E is constricted by observation light during observation for e.g. alignment of the imaging part 3 with the eye E. The fundus photographing optical system 90 of the present embodiment is an optical system for imaging the fundus ER of the eye E to which visible light (daylight color or blue-green light) is projected in order to photograph the fundus ER of the eye E. The fundus observation optical system 80 has an optical axis LC1 and the fundus photographing optical system 90 has an optical axis LC2. The fundus photographing optical system 90 includes the objective lens 31, a first optical-path combining part 32A, a plate glass 33, a second optical-path combining part 34, an imaging diaphragm 35A, a focusing lens 36, an image forming lens 37, an optical-path combining part 38, a field diaphragm 91, a mirror 92, a relay lens 93, a barrier filter part 94, and an imaging device 95. The optical axis LC1 of the fundus observation optical system 80 and the optical axis LC2 of the fundus photographing optical system 90 are made coaxial with each other in a zone from the objective lens 31 to the optical-path combining part 38. That is, the fundus observation optical system 80 and the fundus photographing optical system 90 share an optical path combined by the optical-path combining part 38 in the zone from the objective lens 31 to the optical-path combining part 38. The fundus observation optical system 80 further includes a mirror 81, a relay lens 82, and an imaging device 83 in addition to the components from the objective lens 31 to the optical-path combining part 38 shared by the fundus photographing optical system 90.

The first optical-path combining part 32A is a member for combining optical paths of the first light projecting optical system 10 and the imaging optical system 30. That is, the first optical-path combining part 32A coaxially combines the optical axis LA and the optical axis LC. As the first optical-path combining part 32A, a dichroic mirror, a dichroic prism, and others may be employed. In the present embodiment, the first optical-path combining part 32A is placed between the objective lens 31 and a first image-forming position of the pupil EP of the examinee's eye E (the point denoted with the circular mark in the imaging diaphragm 35A in FIG. 2A). The first image-forming position means a position that is firstly conjugated with each portion of the eye E through the objective lens 31. The position corresponding to the first image-forming position may be referred to as a first conjugate position. In the present embodiment, the first optical-path combining part 32A is provided between the objective lens 31 and the second optical-path combining part 34. The first optical-path combining part 32A of the present embodiment is a dichroic mirror (a wavelength selective mirror) and is located obliquely with respect to the optical axis LC of the imaging optical system 30.

The first optical-path combining part 32A has the property of reflecting light having a center wavelength of 950 nm corresponding to the light (infrared light) to be emitted from an alignment target part 250, and light having a center wavelength of 490 nm corresponding to the light to be emitted from the first light projecting optical system 10. The first optical-path combining part 32A also has the property of transmitting light having a wavelength band or range of 700 to 880 nm corresponding to the light to be emitted from the second light projecting optical system 20, and autofluorescence generated from the fundus by autofluorescence-inducing excitation light projected from the first light projecting optical system 10. Specifically, the first optical-path combining part 32A of the present embodiment reflects the light having a 490-nm center wavelength and the light having a 950-nm center wavelength, while transmits the light having a wavelength band of 700 to 880 nm. The alignment target part 250 is provided on an outer casing of the imaging part 3 and configured to project light to the examinee's eye E not through the objective lens 31. The plate glass 33 is an axial displacement compensating unit for compensating axial displacement of the optical axis LC caused by insertion of the first optical-path combining part 32A into the imaging optical system 30. The plate glass 33 of the present embodiment has a thickness corresponding to the thickness of the first optical-path combining part 32A. The plate glass 33 of the present embodiment has the property of transmitting light having a wavelength band used in observation and photographing. Even though the first optical-path combining part 32A reflects the light with a 490-nm center wavelength, the reflection property for wavelength values apart on a positive side or a negative side may be appropriately set. A first optical-path combining part 32B and a fourth optical-path combining part 49 of the second embodiment mentioned later are also designed to have an appropriately set reflection property for wavelength values apart on a positive side or a negative side.

The first optical-path combining part 32A and the plate glass 33 of the present embodiment are able to move into or out of the imaging optical system 30. To be specific, the first optical-path combining part 32A and the plate glass 33 can be inserted in and removed from the imaging optical system 30 by an inserting/removing unit 270 included in the imaging optical system 30. This inserting/removing unit 270 may be constituted of a solenoid, a cam, and others. Under control of a controller 200, the first optical-path combining part 32A and the plate glass 33 are inserted in an optical path during observation and during autofluorescence photographing and are removed from the optical path during color photographing. The second optical-path combining part 34 is placed between the objective lens 31 and the imaging diaphragm 35A. The second optical-path combining part 34 of the present embodiment is a perforated mirror, which is placed obliquely with respect to the optical axis LC of the imaging optical system 30. This second optical-path combining part 34 is a combining member for combining the optical paths of the imaging optical system 30 and the second light projecting optical system 20. That is, the second optical-path combining part 34 coaxially combines the optical axis LB and the optical axis LC. The second optical-path combining part 34 of the present embodiment has the property of transmitting the light flux from the imaging optical system 30 through an opening provided at the center of the perforated mirror. A mirror part around the opening reflects the light flux coming from the second light projecting optical system 20 toward the optical axis LC so as to travel toward the objective lens 31.

The imaging diaphragm 35A is placed between the second optical-path combining part 34 and the focusing lens 36. The imaging diaphragm 35A is provided on the optical axis LC of the imaging optical system 30 and at the first image-forming position (conjugate position) of the pupil EP of the examinee's eye E through the objective lens 31. The imaging diaphragm 35A serves as an aperture diaphragm for reducing the light flux of the imaging optical system 30. It is to be noted that the structure of an examinee's eye E varies between individuals and thus the conjugate position with the eye E may be determined by use of statistical data of eye structure, data of well-known Gullstrand's model eye, and others. The focusing lens 36 is used to establish a conjugate relationship between the fundus ER of the examinee's eye E and the imaging device 95 (the imaging device 83). The focusing lens 36 is moved by a drive unit 271 in an axial direction of the optical axis LC of the imaging optical system 30. By movement of the focusing lens 36 in the axial direction, the conjugate positional relationship between the fundus ER of the eye E and the imaging device 95 (the imaging device 83) can be adjusted irrespective of the diopter of the examinee's eye E.

The optical-path combining part 38 is a combining member for combining the optical paths of the fundus observation optical system 80 and the fundus photographing optical system 90. That is, the optical-path combining part 38 coaxially combines the optical axis LC1 and the optical axis LC2. The optical-path combining part 38 in the ophthalmic apparatus 100A of the present embodiment is a mirror and is configured to be inserted in and removed from the optical path of the fundus photographing optical system 90 by an inserting/removing unit 272. This inserting/removing unit 272 may be constituted of a solenoid, a cam, and others. The optical-path combining part 38 is not limited to the mirror but also may be another optical-path combining member such as a dichroic mirror, and a half mirror, etc. The barrier filter part 94 is provided between the relay lens 93 and the imaging device 95. The barrier filter part 94 of the present embodiment is used to pick up autofluorescence from the light coming from the examinee's eye E into the objective lens 31 and allow the imaging device 95 to receive the autofluorescence. The barrier filter part 94 of the present embodiment has the property of transmitting light having a wavelength band of 700 to 850 nm and reducing or shielding light having a wavelength other than a wavelength band of 700 to 850 nm. The wavelength property of the barrier filter part 94 is not limited to the above and may be set according to fluorescence to be imaged by the imaging device 95. For instance, the wavelength property of the barrier filter part 94 may be set according to a wavelength of excitation light for fluorescence to be projected to the examinee's eye E. The barrier filter part 94 of the present embodiment is also configured to be inserted in and removed from the optical path of the imaging optical system 30 (the fundus photographing optical system 90) by an inserting/removing unit 273. The inserting/removing unit 273 may be a solenoid and others. The first optical-path combining part 32A of the present embodiment can transmit light having a wavelength band of 700 to 880 nm band and thus is assumed to have a filter property equivalent to that of the barrier filter part 94. Accordingly, since the first optical-path combining part 32A is considered to have the barrier filter function, a barrier filter (the barrier filter part 94) may be placed independently in the imaging optical system 30.

Furthermore, at a position where the barrier filter part 94 is placed in the present embodiment, the barrier filter part 94 allowing passage of only the light having a wavelength band of 700 to 850 nm and a color filter not shown allowing passage of only the light having a wavelength band of 400 to 700 nm may be selectively disposed by the above-described inserting/removing unit 273. With the use of a band pass filter allowing passage of only the light having a wavelength band of 400 to 700 nm, the imaging device 95 can produce a color image of the examinee's eye E with improved color reproducibility as compared with no use of the band pass filter (and the barrier filter part 94). It is to be noted that the band pass filter may be provided to be able to be inserted in and removed from a light projecting optical path (the second light projecting optical system 20 in the present embodiment). The imaging device 95 is provided at a base end of the imaging optical system 30 (the fundus photographing optical system 90). The imaging device 95 of the present embodiment is used as a light receiving unit for performing autofluorescence photographing and normal color photographing of the examinee's eye E (i.e., for receiving the light from the eye E). The imaging device 95 is placed at a position conjugate with the fundus ER of the eye E. The imaging device 95 is a two-dimensional imaging device having sensitivity to visible light and infrared light. The imaging device 95 of the present embodiment is a color image sensor having red, blue, and green color filters arranged in Bayer array just in front of a light receiving section in order to perform autofluorescence photographing and normal color photographing. For instance, when only the autofluorescence photographing (and fluorescence photographing) is to be performed, a monochrome image sensor without color filters may be used.

The imaging device 83 is provided at a base end of the fundus observation optical system 80 branched from (combined with) the optical path shared between the fundus observation optical system 80 and the fundus photographing optical system 90. The imaging device 83 of the present embodiment is used as a light receiving unit for allowing observation of the fundus ER of the examinee's eye E (i.e., for receiving the light from the fundus ER of the eye E). The imaging device 83 is placed in a position conjugate with the fundus ER of the eye E. The imaging device 83 is a two-dimensional imaging device having sensitivity to at least infrared light. The imaging device 83 of the present embodiment is a monochrome image sensor. It is to be noted that the imaging device 83 and the foregoing imaging device 95 may include a CCD (Charge Coupled Device) image sensor or a CMOS (Complementary Metal Oxide Semiconductor) image sensor.

<1-3. Anterior Segment Observation Optical System>

The anterior segment observation optical system 40 of the present embodiment is an optical system for imaging an anterior segment of the examinee's eye E in order to allow observation of the anterior segment of the eye E. The anterior segment observation optical system 40 includes the objective lens 31, the first optical-path combining part 32A, a third optical-path combining part 11, a field lens 41, a relay lens 42, and an imaging device 43. The anterior segment observation optical system 40 and the first light projecting optical system 10 share an optical path combined by the third optical-path combining part 11 and extended in a zone from the objective lens 31 to the third optical-path combining part 11. In other words, the third optical-path combining part 11 coaxially combines the optical axis LA and the optical axis LD. The imaging device 43 is provided at a base end of the anterior segment observation optical system 40. This anterior segment observation optical system 40 including the imaging device 43 of the present embodiment is a light receiving unit for obtaining eye information of the examinee's eye E by a different method from that in the imaging optical system 30. The imaging device 43 of the present embodiment is provided at a position conjugate with the pupil EP of the examinee's eye E. The light (950-nm center wavelength) emitted from a light source of the alignment target part 250 and reflected at a position of the anterior segment of the examinee's eye E enters in the objective lens 31 and then is reflected by the first optical-path combining part 32A and the third optical-path combining part 11 in turn to fall on the imaging device 43. Thus, an anterior segment image of the examinee's eye E is imaged by the imaging device 43. This imaging device 43 is a two-dimensional imaging device having sensitivity to at least infrared light. For instance, the imaging device 43 and the imaging device 83 may be configured as components having the same property. The third optical-path combining part 11 will be explained later.

<1-4. First Light Projecting Optical System>

Figure 6A:
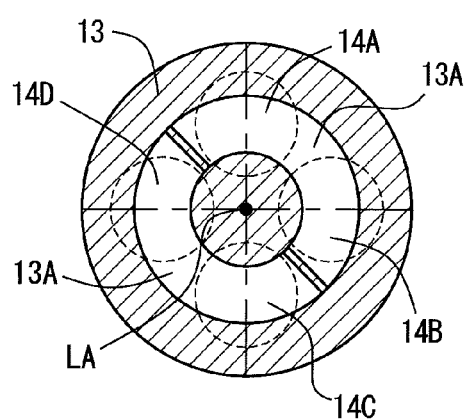
FIGS. 6A and 6B are explanatory views to explain a light restricting part of the first embodiment.

The first light projecting optical system 10 of the present embodiment is an optical system for projecting autofluorescence excitation light (blue-green) to the fundus ER of the examinee's eye E in order to obtain an autofluorescence fundus image of the eye E. The first light projecting optical system 10 of the present embodiment includes the objective lens 31, the first optical-path combining part 32A, the third optical-path combining part 11, a first light restricting part 12, a light restricting part 13, and a first light source 14. The light restricting part 13 is placed at a position conjugate with the pupil EP of the examinee's eye E. In more detail, the light restricting part 13 is located at the first image-forming position of the pupil EP of the examinee's eye E through the objective lens 31. The light restricting part 13 is made of a perforated plate-like member formed with ring-shaped (a combination of half-round ring shapes in the present embodiment) openings 13A (see FIG. 6A). In FIG. 6A, LEDs (14A to 14D) of the first light source 14 are indicated with dotted lines. The first light source 14 will be mentioned later. A part of the light emitted from the LEDs 14A to 14D of the first light source 14 is shielded and another part of the same passes through the openings 13A of the light restricting part 13 (see FIG. 6B). In the present embodiment, the light restricting part 13 has an axial symmetrical shape and thus a distance T1 (a distance between the photographing axis LA and the inner circumference of one opening 13A) and a distance T2 (a distance between the inner circumference and the outer circumference of one opening 13A in a radial direction) are uniform circumferentially in one opening 13A. The same distance relationship applies to the other opening 13A. The light restricting part 13 may be made of a glass plate subjected to an etching process the like.

Figure 6B:
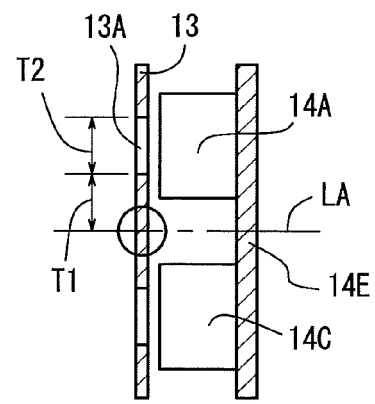
Figure 9:
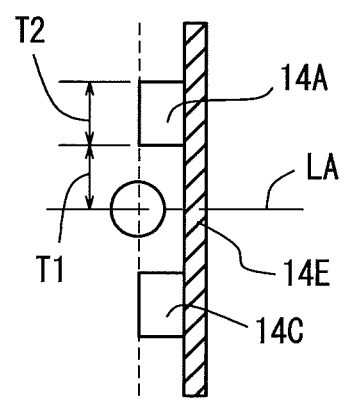
FIG. 9 is an explanatory view to explain a modified example of a first light source.

In the present embodiment, the light restricting part 13 and the first light source 14 are combined, but not limited thereto. For instance, a first light source 14 including a light restricting part 13 may be employed. FIG. 9 shows a modified example of the first light source 14. In the present embodiment, the dimension of an emission opening of the first light source 14 is determined as shown in FIGS. 6A and 6B. In the example shown in FIG. 9, on the other hand, the first light source 14 is configured such that the distance T1 from the optical axis LA and the distance T2 of an emission opening are equal to those in the present embodiment shown in FIGS. 6A and 6B at a position conjugate with the pupil EP of the examinee's eye E. The light sources in FIG. 9 are selected LEDs each having an emission opening having a distance T2 or less and arranged on a support base 14E (a circuit board or the like) so that an end of an emission opening of each of the LEDs (on the optical axis LA side)

is equal to the distant T1 from the optical axis LA. Accordingly, the first light source 14 in the example of FIG. 9 includes the light restricting part 13. In this example of FIG. 9, the frames or opening support base of the LEDs form the light restricting part 13. Needless to say, the first light source 14 may be configured to include the light restricting part 13 by the emission angle characteristics of the LEDs including a lens function (a light beam changing unit), so-called a lens-equipped LED.

The placement of the first light source 14 including the light restricting part 13 is not limited to the position conjugate with the pupil EP of the examinee's eye E. For instance, the first light source 14 may be configured at a distance T1A longer than the distance T1 in the present embodiment and placed at a position so that an end (an emission side) of the emission opening is located close to a cornea EC than the pupil EP of the eye E. Specifically, it is only necessary to place the first light source 14 to avoid overlapping of projection light (light beam PA and light beam PB in FIGS. 3A and 3B) and imaging light (light beam S in FIGS. 3A and 3B) at the position of the pupil EP of the examinee's eye E. It is to be noted that the configurations of the light restricting part 13 and the first light source 14 and the configuration of the first light source 14 including the light restricting part 13 are not limited to those in the present embodiment. For instance, the distance T2 may be elongated in a direction away from the optical axis LA. In this case, however, it is conceived that an iris of the examinee's eye E is apt to block light. As another alternative, a light source part of the first light source 14 may be constituted of a plurality of LEDs each having an emission opening shorter than the distance T2 and being arranged in a matrix or honeycomb pattern.

Figure 5:
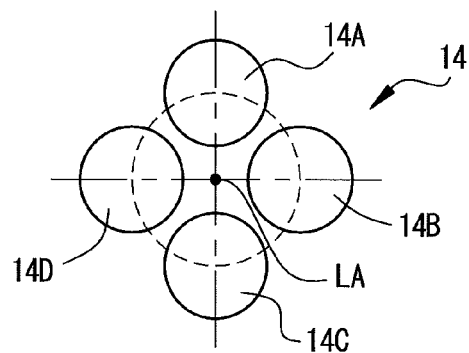
FIG. 5 is an explanatory view to explain a first light source of the first embodiment.

The first light source 14 is placed at a base end of the first light projecting optical system 10. The first light source 14 in the present embodiment is a light source for emitting excitation light to perform autofluorescence photographing. The first light source 14 of the present embodiment is placed between the position conjugate with the pupil EP of the examinee's eye E and a position conjugate with an apex of the cornea EC of the examinee's eye E. The first light source 14 of the present embodiment includes a plurality of LEDs (Light Emitting Diodes) 14A to 14D each placed apart from the optical axis LA of the first light projecting optical system 10 (see FIG. 5). The first light source 14 of the present embodiment is placed so that the plurality of LEDs are arranged in a circle centered on the optical axis LA of the first light projecting optical system 10 and in an axial symmetric relation about the optical axis LA. The LEDs employed as the first light source 14 of the present embodiment each have a center wavelength of 490 nm. Four LEDs of the same type are used herein. The first light source 14 is not limited to the LEDs and may be provided for example by a combination of a xenon flash lamp(s) and an optical filter(s).

Figure 7:
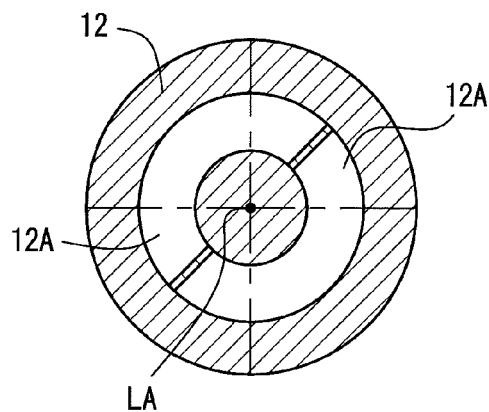
FIG. 7 is an explanatory view to explain a first light restricting part of the first embodiment.

The first light restricting part 12 is provided between the light restricting part 13 and the first optical-path combining part 32A. This light restricting part 12 of the present embodiment is an unwanted light suppressing unit for reducing unwanted light (reflection light or fluorescence) which may arise in a crystalline lens EL of the examinee's eye E. The first light restricting part 12 of the present embodiment is placed at a position conjugate with a rear end (a retina side) of the crystalline lens EL of the examinee's eye E. The light restricting part 12 is made of a perforated plate-like member formed with a ring-shaped (a combination of half-round ring shapes in the present embodiment) opening 12A (see FIG. 7).

In the present embodiment, the light emitted from the first light source 14 is projected to the examinee's eye E via the light restricting part 13, the first light restricting part 12, the third optical-path combining part 11, and the objective lens 31. It is to be noted that the light emitted from the first light source 14 toward the first optical-path combining part 32A is reflected toward the objective lens 31 by the property of the dichroic mirror constituting the first optical-path combining part 32A. When the light emitted from the first light source 14 is reflected by the first optical-path combining part 32A, the optical axis LA of the first light projecting optical system 10 and the optical axis LC of the imaging optical system 30 are made coaxial and then projected to the examinee's eye E. The light to be projected to the examinee's eye E by the first light projecting optical system 10 has a wavelength (a first wavelength λ1) having a center wavelength of 490 nm. In the ophthalmic apparatus 100A of the present embodiment, the light with the first wavelength λ1 is projected as fluorescence excitation light to the examinee's eye E, so that autofluorescence occurring in the eye E is imaged by the imaging device 95 of the imaging optical system 30. The ophthalmic apparatus 100A of the present embodiment is configured such that the imaging device 95 images the light having a wavelength band of 700 to 850 nm passing through the barrier filter part 94 as autofluorescence occurring in the examinee's eye E. In other words, by use of the light having a 490-nm center wavelength from the first light source 14 as excitation light, the fundus information of the examinee's eye E is obtained with the imaging device 95 through the barrier filter part 94. In the case of using the first light source 14, an autofluorescence image is obtained as the fundus information of the examinee's eye E.

The third optical-path combining part 11 is provided between the first light restricting part 12 and the first optical-path combining part 32A, that is, between a position conjugate with a crystalline-lens back surface EL1 of the examinee's eye E and a position conjugate with the fundus ER. The third optical-path combining part 11 is provided obliquely to the optical axis LA of the first light projecting optical system 10. The third optical-path combining part 11 is a member for combining the optical paths of the first light projecting optical system 10 and the anterior segment observation optical system 40. In other words, the third optical-path combining part 11 coaxially combines the optical axis LA and the optical axis LD. In the present embodiment, a dichroic mirror (a wavelength selective mirror) is used as the third optical-path combining part 11. This third optical-path combining part 11 has the property of reflecting the light with a center wavelength of 950 nm corresponding to the light emitted from the alignment target part 250 and transmitting the light with a center wavelength of 490 nm corresponding to the light emitted from the first light source 14. Specifically, the third optical-path combining part 11 in the present embodiment reflects the light having a wavelength band centered at 950 nm and transmits the light having a wavelength band centered at 490 nm. By the property of the third optical-path combining part 11, the light traveling from the first light source 14 toward the first optical-path combining part 32A passes through the third optical-path combining part 11. On the other hand, the light entering in the objective lens 31 and traveling in a direction from the first optical-path combining part 32A to the third optical-path combining part 11 is reflected by this third optical-path combining part 11 and goes toward the imaging device 43. In the ophthalmic apparatus 100A of the present embodiment, as described above, the imaging optical system for imaging a portion different from the fundus ER of the examinee's eye E is shared by the optical path branched from the imaging optical system 30 to project light to the fundus ER of the examinee's eye E. Thus, the imaging part 3 can be simplified in structure.

<1-5. Second Light Projecting Optical System>

The second light projecting optical system 20 of the present embodiment is an optical system for projecting infrared light or visible light (daylight color light) to the fundus ER of the examinee's eye E in order to obtain an observation image and a color photographed image of the fundus ER of the examinee's eye E. Specifically, the second light projecting optical system 20 projects the light having a second wavelength different from the light (light having the first wavelength) projected by the first light projecting optical system 10 to the examinee's eye E in order to obtain the fundus information of the eye E. The second light projecting optical system 20 includes an observation illumination optical system 50, a photographing illumination optical system 60, and a target projection optical system 70. The observation illumination optical system 50 of the present embodiment is an optical system for projecting infrared light to the fundus ER of the examinee's eye E. The photographing illumination optical system 60 of the present embodiment is an optical system for projecting visible light (daylight color light) to the fundus ER of the examinee's eye E. The target projection optical system 70 of the present embodiment is an optical system for projecting a target for focusing to the fundus ER of the examinee's eye E. The target (light) for focusing used herein is infrared light. The observation illumination optical system 50 has an optical axis LB1, the photographing illumination optical system 60 has an optical axis LB2, and the target projection optical system 70 has an optical axis LB3.

The photographing illumination optical system 60 of the present embodiment includes the objective lens 31, the first optical-path combining part 32A, the plate glass 33, the second optical-path combining part 34, a third light restricting part 21, a relay lens 22, a black-spot plate 23, a focus target combining part 24, a relay lens 25, a light restricting part 26, a fourth light restricting part 27, and a second light source 28. The photographing illumination optical system 60 of the present embodiment is a light projecting unit for projecting light having a wavelength different from that in the first light projecting optical system 10 to perform normal color photographing of the examinee's eye E. The second light source 28 is placed at a base end of the photographing illumination optical system 60. The second light source 28 of the present embodiment is placed between a second image-forming position conjugate with the pupil EP of the examinee's eye E and a second image-forming position conjugate with the cornea EC. The second image-forming position (the second conjugate position) is a position providing a second conjugate relationship with the examinee's eye E through the objective lens 31 and the relay lens (the relay lens 22 and the relay lens 25). The second light source 28 of the present embodiment employs a xenon flash lamp. The flash lamp of the present embodiment is formed of a pipe bent in an annular form, so that the lighting shape of the second light source 28 is annular. The xenon flash lamp of the present embodiment employs a transparent material (hard glass or quartz glass) as an emission part. Thus, the light emitted from a light source 52A provided at a base end of an observation illumination optical system 50 mentioned later passes (transmits) through the second light source 28. In the present embodiment, the photographing illumination optical system 60 employing the second light source 28 projects, onto the examinee's eye E, the light (a second wavelength $\lambda 2$ different from the first wavelength $\lambda 1$) including at least a wavelength band of 400 to 700 nm.

The fourth light restricting part 27 is placed between the second light source 28 and the light restricting part 26. The fourth light restricting part 27 is provided at a position conjugate with the pupil EP of the examinee's eye E. The fourth light restricting part 27 of the present embodiment is an unwanted light suppressing unit for reducing unwanted light (reflection light or fluorescence) which may arise inside the examinee's eye E. The fourth light restricting part 27 is a perforated plate-like member formed with a ring-shaped (a combination of half-round ring shapes in the present embodiment) opening. The light restricting part 26 is placed between the fourth light restricting part 27 and the relay lens 25. The light restricting part 26 is provided at a position conjugate with a back surface EL1 (on a retina side) of the crystalline lens EL of the examinee's eye E through the objective lens 31. The light restricting part 26 is an unwanted light suppressing unit for reducing unwanted light (reflection light or fluorescence) which may arise in the crystalline lens EL of the examinee's eye E. The light restricting part 26 is a perforated plate-like member formed with a ring-shaped (a combination of half-round ring shapes in the present embodiment) opening. The relay lens 25 is positioned between the light restricting part 26 and the focus target combining part 24. The light passing through the fourth light restricting part 27 is collimated into nearly parallel light by the relay lens 25 and then travels toward the second optical-path combining part 34.

The focus target combining part 24 is provided between the relay lens 25 and the black-spot plate 23. The focus target combining part 24 is provided obliquely to the optical axis LB of the second light projecting optical system 20. The focus target combining part 24 reflects a focus target (infrared light) coming from off-axis to on-axis of the second light projecting optical system 20 so that the focus target goes toward the second optical-path combining part 34. The focus target combining part 24 combines the optical paths of the target projection optical system 70 and the second light projecting optical system 20. In other words, the focus target combining part 24 coaxially combines the optical axis LB3 and the optical axis LB. The focus target combining part 24 is able to be inserted in or removed from the second light projecting optical system 20 by an actuator and a drive mechanism not shown. Further, the focus target combining part 24 is also able to move between the relay lens 25 and the black-spot plate 23 in a direction of the optical axis LB of the second light projecting optical system 20. The focus target combining part 24 is moved in an axial direction of the second light projecting optical system 20 in sync with axial movement of the focusing lens 36 of the imaging optical system 30. The light source of the focus target light (infrared light) provided in the target projection optical system 70 and the focus target combining part 24 are constituted in the form of a single unit. Accordingly, when the focus target combining part 24 is moved in the axial direction, a projection position (an image forming position) of the focus target to be projected to the fundus ER of the examinee's eye E through the objective lens 31 changed. In other words, when the focus target combining part 24 is moved in the optical axis direction, the focus target is projected to different positions in the optical axis direction of the optical axis LC of the imaging optical system 30 (e.g., see Japanese patent unexamined application publication No. S55(1980)-96138).

The black-spot plate 23 is provided between the focus target combining part 24 and the relay lens 22. The black-spot plate 23 is a glass plate having a surface formed with a small circular black spot at a position which the optical axis LB of the second light projecting optical system 20 will pass through. The black-spot plate 23 serves to suppress a phenomenon that, when the light projected by the second light projecting optical system 20 passes through the objective lens 31, the light reflecting by the surface or the inner surface of the objective lens 31 travels toward the imaging device 95, resulting in artifacts appearing in a photographed image (e.g., see Japanese patent examined publication No. S47(1972)-44645). It is to be noted that it is conceived that no fluorescence occurs even when excitation light is projected (transmitted) to a lens such as the objective lens 31 and others. Accordingly, the black-spot plate 23 is conceived to be effective in suppressing artifacts (appearance due to reflection by an optical system component) in non-fluorescence photographing. The relay lens 22 is explained below. This relay lens 22 is provided between the black-spot plate 23 and the third light restricting part 21. The relay lens 22 forms once an image of the light collimated into nearly parallel light (projection light passing through the fourth light restricting part 27) by the relay lens 25, at a position between the relay lens 22 and the second optical-path combining part 34. The third light restricting part 21 is provided between the relay lens 22 and the second optical-path combining part 34. The third light restricting part 21 of the present embodiment is provided at a position conjugate with the apex of the cornea EC of the examinee's eye E. The third light restricting part 21 is made of a perforated plate-like member formed with a ring-shaped (annular) opening. When photographing is to be performed using the second light source 28, the first optical-path combining part 32A located on the optical axis LB1 of the photographing illumination optical system 60 is removed (retracted) from the optical axis LB1.

Successively, the observation illumination optical system 50 will be explained. The optical axis LB1 of the observation illumination optical system 50 and the optical axis LB2 of the photographing illumination optical system 60 are made coaxial with each other. The observation illumination optical system 50 of the present embodiment projects infrared light (having the second wavelength λ2 different from the first wavelength λ1) to the fundus ER of the examinee's eye E. The observation illumination optical system 50 shares some components from objective lens 31 to the second light source 28 with the photographing illumination optical system 60. Differences are explained below. The light source 52A is provided at a base end of the observation illumination optical system 50. The light source 52A of the present embodiment is a halogen lamp. In the present embodiment, the light source 52A has only to emit at least infrared light. For instance, the light source 52A may be an infrared LED. A condenser lens 51 is provided between the light source 52A and the second light source 28. The condenser lens 51 condenses the light emitted from the light source 52A to go toward the second light source 28. The condenser lens 51 of the present embodiment has been subjected to coating treatment to allow passage of only infrared wavelength (infrared component). In the present embodiment, the condenser lens 51 passes the light having a wavelength band of 700 to 880 nm as infrared wavelength. Since the emission part of the second light source 28 is made of transparent material, the light condensed by the condenser lens 51 transmits the second light source 28, thus traveling travels toward the fourth light restricting part 27. Since the first optical-path combining part 32A transmits the light having a wavelength band of 700 to 880 nm, the first optical-path combining part 32A located on the optical axis LB2 of the observation illumination optical system 50 is kept inserted in the optical axis LB1 during observation using the second light source 28.

The imaging part 3A of the ophthalmic apparatus 100A of the present embodiment includes, as explained above, an imaging unit for performing fundus observation, normal color photographing, autofluorescence photographing, and anterior segment observation. The fundus observation is performed in such a way as to project the light having a wavelength band of 700 to 880 nm to the examinee's eye E by use of the observation illumination optical system 50 (the second light projecting optical system 20), and obtain a fundus observation image from the light having a wavelength band of 700 to 880 nm by use of the fundus observation optical system 80 (the imaging optical system 30). The normal color photographing is performed in such a way as to project the light having a wavelength band of 400 to 700 nm to the examinee's eye E by use of the optical axis illumination optical system 60 (the second light projecting optical system 20), and obtain a fundus photographed image from the light having a wavelength band of 400 to 700 nm by use of the fundus photographing optical system 90 (the imaging optical system 30). Further, the autofluorescence photographing is performed in such a way as to project the light with a center wavelength of 490 nm as autofluorescence excitation light to the examinee's eye E by use of the first light projecting optical system 10, and obtain an auto-fluorescence fundus image from the light having a wavelength band of 700 to 850 nm by use of the fundus photographing optical system 90 (the imaging optical system 30). The anterior segment observation is performed in such a way as to project the light with a center wavelength of 950 nm to the examinee's eye E by use of the light source of the alignment target part 250, and obtain an anterior segment observation image of the examinee's eye E from the light with a center wavelength of 950 nm by use of the anterior segment observation optical system 40.

<1-6. Removal of Unnecessary Light>

Subsequently, an explanation is given to a method of removing unnecessary or unwanted light (fluorescence and reflection light from an unnecessary portion) of the present embodiment referring to FIGS. 3A and 3B. FIGS. 3A and 3B are conceptual diagrams to explain a state of projection light (light beam PA and light beam PB) from the first light projecting optical system 10 and imaging light (light beam S) from the imaging optical system 30 in the anterior segment and the inside of the examinee's eye E. FIG. 3A shows a case where the first light restricting part 12 is provided in the first light projecting optical system 10 and FIG. 3B shows a case where the first light restricting part 12 is not provided in the first light projecting optical system 10. An image A is an image of the light restricting part 13. An image B is an image of the first light restricting part 12. Images C1 and C2 are images of the first light source 14. An image D is an image of an imaging diaphragm 35A. In FIGS. 3A and 3B, the images C1 and C2 are formed by the surface light sources constituting the first light source 14, which are arranged separately and have a width (range). As already explained, the optical axis LA of the first light projecting optical system 10 and the optical axis LC of the imaging optical system 30 are combined coaxially by the first optical-path combining part 32A. Accordingly, the images A, B, C (C1 and C2), and D are arranged coaxially. Solid lines represent the imaging light (light beam S) to be used in imaging by the imaging optical system 30. As shown in FIGS. 3A and 3B, the light emitted from the fundus ER including peripheral portions (ER1, ER2) is narrowed or reduced by the imaging diaphragm 35A (image D), and the light passing through the imaging diaphragm 35A (image D) becomes widened and enters in the objective lens 31.

Broken lines represent projection light (light beam PA, light beam PB) to be used for projecting light to the fundus ER by the first light projecting optical system 10. As shown in FIGS. 3A and 3B, the light condenses once at a position of the images C (images C1 and C2) corresponding to the images of the first light source 14, and then travels from the position of the images C toward the fundus ER. With the light restricting part 13 (image A), the lights of the first light source 14 traveling from the position of the images C toward the fundus ER are restricted from widening. In FIG. 3A, furthermore, the lights of the first light source 14 traveling from the position of the images C toward the fundus ER are restricted by the light restricting part 13 (image A) from widening and additionally restricted by the first light restricting part 12 (image B) from widening. Comparing FIGS. 3A and 3B, intersecting regions U of the projection lights (light beam PA, light beam PB) and the imaging light (light beam S) in the crystalline lens EL of the examinee's eye E change according to the presence or absence of the first light restricting part 12 (image B). To be more specific, in FIG. 3B, the regions U are generated by intersection of the projection lights (light beam PB) and the imaging light (light beam S).

When excitation light is projected to the examinee's eye E, a portion of the eye E in which autofluorescence occurs is not limited to the fundus ER. According to the present embodiment, the imaging diaphragm part 35 (image D) of the imaging optical system 30 and the light restricting part 13 (image A) of the first light projecting optical system 10 suppress intersection of the projection lights (light beam PA, light beam PB) and the imaging light (light beam S) inside the examinee's eye E. In the present embodiment, focusing attention on the possibility that the autofluorescence occurs in the crystalline lens EL of the examinee's eye E, the image B of the first light restricting part 12 prevents disadvantageous superimposing of the autofluorescence occurring in the crystalline lens EL on the autofluorescence image of the fundus ER. To be specific, zones indicated as the regions U in FIG. 3B are reduced. This can suppress unwanted fluorescence or reflection caused in a portion other than the fundus ER to obtain appropriate fundus image (fundus fluorescence information). In the present embodiment, since the images C of the first light source 14 are formed between the pupil EP of the examinee's eye E and the apex of the cornea EC, the light emitted from the images C of the first light source 14 can be efficiently passed through the image A of the light restricting part 13, and thus projected efficiently to the fundus ER of the examinee's eye E.

The degree of autofluorescence occurring in the crystalline lens EL is conceived to vary according to the internal structure of the examinee's eye E. For instance, if the crystalline lens EL is thick, autofluorescence occurring in the crystalline lens EL is conceived to be apt to superimpose on the autofluorescence image of the fundus ER. Further, the superimposing degree of autofluorescence is considered to vary according to opacity degree of the crystalline lens EL. It is also conceived that the degree of autofluorescence occurring in the crystalline lens EL varies according to the wavelength of autofluorescence excitation light to be used. Moreover, the degree of appearance of the autofluorescence occurring in the crystalline lens EL also varies according to the field angle (the range of a retina of the fundus ER from which the autofluorescence is obtained) of the imaging optical system 30. Accordingly, there is a conceivable case where the first light projecting optical system 10 does not need to include the first light restricting part 12 and the light restricting part 13. As another alternative, at least either of the first light restricting part 12 or the light restricting part 13 may be configured to be inserted in and removed from the optical path of the first light projecting optical system 10. As still another alternative, at least either of the first light restricting part 12 or the light restricting part 13 may be configured as a light beam changing unit such as an iris diaphragm. In the present embodiment, the first light restricting part 12 is provided at a position conjugate with the back surface EL1 of the crystalline lens EL of the examinee's eye E, but not limited thereto. The first light restricting part 12 has only to be provided anywhere between a position conjugate with the pupil EP and a position conjugate with the fundus ER of the examinee's eye E. That is, the first light restricting part 12 is required only to restrict the projection light traveling toward the optical axis LC of the imaging optical system 30, from the position apart from the optical axis LC.

In the ophthalmic apparatus 100A of the present embodiment, the first light source 14 is provided at the first image-forming position of the examinee's eye E, so that the lights of the first light source 14 to be used for autofluorescence are effectively guided to the fundus ER. For instance, the second light projecting optical system 20 includes the black-spot plate 23 for suppressing internal reflection of the objective lens 31 on the optical path relayed by the relay lenses (the relay lens 22 and the relay lens 25). Accordingly, the second light source 28 of the second light projecting optical system 20 is provided ahead of the second image-forming position of the pupil EP. The light emitted from the second light source 28 of the second light projecting optical system 20 has to pass through many lenses and many light restricting parts and thus is reduced. On the other hand, the lights emitted from the first light source 14 of the first light projecting optical system 10 do not have to pass through for example the black-spot plate 23 and the relay lenses. Thus, the lights emitted from the first light source 14 can be projected efficiently to the fundus ER of the examinee's eye E.

The ophthalmic apparatus 100A of the present embodiment is provided with more than one type of light projecting optical systems for projecting light to the fundus ER. The first light projecting optical system 10 is a light projecting optical system for fluorescence photographing likely to need a large amount of light (likely to need a larger amount of light to be projected than an amount of light projected to the examinee's eye E during non-fluorescence photographing). The second light projecting optical system 20 is a multi-functional light projecting optical system. For instance, the second light projecting optical system 20 is provided with the black-spot plate 23 that reduces reflection on the surface and the internal surface of the objective lens 31 which is liable to cause defects during non-fluorescence photographing. Further, the second light projecting optical system 20 is provided with the target projection optical system 70 for projecting a special target for focusing to the fundus ER of the examinee's eye E. Moreover, the second light projecting optical system 20 is provided with the third light restricting part 21 for reducing unwanted reflection light that reflects on the cornea EC of the examinee's eye E. Still further, the second light projecting optical system 20 includes the fundus observation optical system 80 for allowing observation of the fundus ER of the examinee's eye E with infrared light. As above, since the lights (light beams) are projected to the fundus ER of the examinee's eye E by different ways from more than one projecting optical path, for example, it is possible to avoid the necessity of complicated or expensive light sources for fluorescence photographing. Thus, an appropriate fundus image can be obtained even by a simple structure.

In a case where the lights of a plurality of wavelengths including non-fluorescence photographing and fluorescence photographing are projected to image the fundus ER of the examinee's eye E corresponding to each of the projected wavelengths, the reflection light amount (fluorescence amount) from the fundus ER varies according to the projected wavelengths. Depending on the projected wavelength, unwanted light (reflection light or fluorescence) arising from a portion other than the fundus ER is different. Moreover, since the objective lens 31 is shared, and the target projection optical system for focusing and the anterior segment imaging optical system described in the embodiment are installed, the optical paths of the illumination optical systems are complicated. Therefore, the numerical aperture (NA) of the light projecting optical systems to project light to the fundus ER of the examinee's eye E may depend on the placement of optical members having optical functions sharing the objective lens 31 or the component placement (lens power allocation) with consideration of adjustability for adjusting in assembling each of the optical members constituting respective optical functions. In the present embodiment, the ophthalmic apparatus 100A includes a plurality of light projecting optical systems for projecting light to the fundus ER of the examinee's eye E, so that the flexibility of the numerical aperture (NA) of the light projecting optical systems increases as compared with the case of projecting light from a single light projecting optical system to the fundus ER of the examinee's eye E. Accordingly, light projection can be achieved by use of the light projecting optical system with an appropriate numerical aperture (NA) according to the wavelength to be projected to the examinee's eye E, so that the light emitted from the light source can be efficiently projected to the examinee's eye E. For instance, as compared with the case of using only one light projecting optical system, available light sources are increased. To be specific, the NA of the first light projecting optical system 10 of the present embodiment is a larger value than the NA of the second light projecting optical system 20. Thus, available types of light sources to be used in the first light projecting optical system 10 are increased and each light source itself can be reduced in capacity. Consequently, the low-cost ophthalmic apparatus 100A capable of performing fluorescence photographing can be provided without being limited by NA of the light projecting optical system capable of performing non-fluorescence photographing. In a case of using an LED or LEDs as the light source of fluorescence excitation light, particularly, available choices of LEDs are suitably increased because the first light projecting optical system 10 of the present embodiment has a large NA. For instance, in a case of projecting autofluorescence excitation light from the second light projecting optical system 20, the second light projecting optical system 20 needs to include a filter for generating excitation light and a drive mechanism for inserting/removing the filter. In the present embodiment, on the other hand, the first light source 14 of the first light projecting optical system 10 includes the LEDs and the first light source 14 itself lights up with a wavelength of fluorescence excitation light. Specifically, the light projecting optical system for projecting autofluorescence excitation light does not need to include a filter and a drive mechanism for generating the autofluorescence excitation light. Thus, the ophthalmic apparatus 100A can be provided at low cost and with little possibility of breakage.

<1-7. Control System>

The imaging device 43, the imaging device 83, the imaging device 95, the inserting/removing unit 270, the drive unit 271, the inserting/removing unit 272, the inserting/removing unit 273 are connected to the controller 200. The controller 200 displays, on the monitor 8, the anterior segment observation image imaged by the imaging device 43, the fundus observation image imaged by the imaging device 83, and the fundus photographed image imaged by the imaging device 95. That is, the controller 200 serves as a display control unit for imaged images. To the controller 200, there are further connected the XYZ actuator 6, a movement mechanism 210, an inserting/removing mechanism 220, the rotary knob 4a, the photographing switch 4b, a switch part 230 having various switches, a memory serving as a storage unit 240, each light source, and others.

<1-8. Use Method>

A use method of the ophthalmic apparatus 100A configured as above will be explained below. Firstly, the autofluorescence photographing is explained. Upon power-on, the controller 200 performs an initializing operation of for example a presenting position of fixation targets, and others. The fixation-target presenting position can be changed when an examiner operates a predetermined visual-line direction changing switch provided in the switch part 230. At an initial stage, the first optical-path combining part 32A and the optical-path combining part 38 are inserted in the optical path of the imaging optical system 30, and the focus target combining part 24 is inserted in the optical path of the second light projecting optical system 20.

After completion of the initializing operation, the controller 200 turns on the light source of the alignment target part 250 to project infrared light to the anterior segment of the examinee's eye E. The controller 200 displays, on the monitor 8, the anterior segment observation image based on an output signal of the imaging device 43 imaging the anterior segment of the examinee's eye E. The examiner operates a photographing mode selection switch provided in the switch part 230 to select the autofluorescence photographing mode. When the controller 200 detects that the autofluorescence photographing mode is selected by the examiner, the controller 200 inserts the barrier filter part 94 into the optical path of the imaging optical system 30 (the fundus photographing optical system 90).

The examiner requests the examinee to put his/her head on the head support part 5. While observing the anterior segment observation image displayed on the monitor 8, the examiner operates the joystick 4 to move the imaging part 3 to right and left, and up and down to align the examinee's eye E and the imaging part 3. The examiner presses a changeover switch not shown provided in the switch part 230. Upon detecting that the changeover switch has been pressed, the controller 200 changes over the signal to be used for display on the monitor 8 from the output signal of the imaging device 43 to an output signal of the imaging device 83. In association with this control, the image displayed on the monitor 8 is changed from the anterior segment observation image based on the output signal of the imaging device 43 to the fundus observation image based on the output signal of the imaging device 83. Further, the controller 200 turns on the light source 52A. The examiner confirms that the focus target superimposed on the fundus observation image and operates a predetermined focusing knob provided on the switch part 230 to make focus adjustment. When detecting the operation of the switch part 230, the controller 200 drives the image forming lens 37 and the focus target combining part 24 in respective axial directions. When this focus adjustment is performed by the examiner, the fundus ER of the examinee's eye E and the imaging device 95 (imaging device 83) come into a conjugate positional relationship.

Subsequently, the examiner presses the photographing switch 4b. When detecting the photographing switch 4b is pressed, the controller 200 outputs a photographing start signal. The controller 200 moves the optical-path combining part 38 and the focus target combining part 24 out of the optical path of the imaging optical system 30 and also turns off the light source of the alignment target part 250 and the light source 52A. The controller 200 successively turns on the first light source 14 to project excitation light for autofluorescence to the fundus ER of the examinee's eye E. The autofluorescence occurring in the fundus ER and others is received by the imaging device 95 through the optical components of the imaging optical system 30, such as the objective lens 31 and the barrier filter part 94. The controller 200 displays, on the monitor 8, the autofluorescence fundus image based on an output signal of the imaging device 95. The controller 200 further stores image date of the autofluorescence fundus image generated based on the output signal of the imaging device 95 in the storage unit 240.

Next, the normal color photographing is explained. This normal color photographing is fundus color photographing widely used as general fundus imaging and visible light photographing to project light having a wavelength band of 400 to 700 nm and photograph reflection light having the same wavelength band. After completion of the above-described initializing operation, the controller 200 turns on the light source of the alignment target part 250, so that the anterior segment illumination light (infrared light) is projected to the examinee's eye E. The controller 200 displays, on the monitor 8, the anterior segment observation image based on the output signal of the imaging device 43 that imaged the anterior segment of the examinee's eye E. The examiner operates the photographing mode selection switch provided in the switch part 230 to select the normal color photographing mode. Since the normal color photographing mode is selected, the barrier filter part 94 is held outside the optical path of the imaging optical system 30 (fundus photographing optical system 90).

The examiner requests the examinee to put his/her head on the head support part 5. While observing the anterior segment observation image displayed on the monitor 8, the examiner operates the joystick 4 to move the imaging part 3 to right and left, and up and down to align the examinee's eye E and the imaging part 3. The examiner presses a changeover switch not shown provided in the switch part 230. Upon detecting that the changeover switch has been pressed, the controller 200 changes over the signal to be used for display on the monitor 8 from the output signal of the imaging device 43 to an output signal of the imaging device 83. In association with this control, the image displayed on the monitor 8 is changed from the anterior segment observation image based on the output signal of the imaging device 43 to the fundus observation image based on the output signal of the imaging device 83. Further, the controller 200 turns on the light source 52A. The examiner confirms that the focus target superimposed on the fundus observation image and operates a predetermined focusing knob provided on the switch part 230 to make focus adjustment. When detecting the operation of the switch part 230, the controller 200 drives the image forming lens 37 and the focus target combining part 24 in respective axial directions. When this focus adjustment is performed by the examiner, the fundus ER of the examinee's eye E and the imaging device 95 (imaging device 83) come into a conjugate positional relationship.

Subsequently, the examiner presses the photographing switch 4b. When detecting the photographing switch 4b is pressed, the controller 200 outputs a photographing start signal. The controller 200 moves (retracts) the first optical-path combining part 32A, the optical-path combining part 38 and the focus target combining part 24 out of the optical path of the imaging optical system 30 and also turns off the light source of the alignment target part 250 and the light source 52A. The controller 200 successively turns on the second light source 28 to project visible light having a wideband (a wavelength band of 400 to 700 nm) to the fundus ER of the examinee's eye E. The reflected light by the fundus ER, of the normal visible light, is received by the imaging device 95 through the optical components of the imaging optical system 30 such as the objective lens 31. The controller 200 displays the normal color fundus image based on the output signal of the imaging device 95 on the monitor 8. The controller 200 further stores image date of the normal color fundus image generated based on the output signal of the imaging device 95 in the storage unit 240.

2. Second Embodiment

Next, a second embodiment of the ophthalmic apparatus will be explained, referring to FIGS. 4A and 4B.

<2-1. Configuration>

An ophthalmic apparatus 100B of the second embodiment differs in only an imaging part from the ophthalmic apparatus 100A of the first embodiment. Thus, an imaging part 3B (optical systems and a control system) of the ophthalmic apparatus 100B will be explained below. It is to be noted that the same reference signs as those in FIGS. 2A and 2B showing the ophthalmic apparatus 100A of the first embodiment denote identical parts or components to those in the ophthalmic apparatus 100A. Their explanations are thus omitted. The optical systems in the ophthalmic apparatus 100B of the second embodiment include the first light projecting optical system 10, the second light projecting optical system 20, the imaging optical system 30, the anterior segment observation optical system 40, and a fixation target presenting optical system.

<2-2. Imaging Optical System>

The imaging optical system 30 of the present embodiment is an optical system for imaging the fundus ER of the examinee's eye E. The imaging optical system 30 of the present embodiment is used as both an optical system for allowing observation of the fundus ER of the examinee's eye E to which infrared light (substantially colorless) is projected and an optical system for photographing the fundus ER of the examinee's eye E to which visible light (blue-green) is projected. The imaging optical system 30 of the present embodiment includes the objective lens 31, a fourth optical-path combining part 89, the first optical-path combining part 32B, an imaging diaphragm 35B, the focusing lens 36, the image forming lens 37, an optical-path combining part 87, the barrier filter part 94, and the imaging device 95. The optical-path combining part 87 combines the optical path of the imaging optical system 30 and the optical path of the fixation target presenting optical system. In other words, the optical-path combining part 87 coaxially combines the optical axis LC and an optical axis of the fixation target presenting optical system. The optical-path combining part 87 of the present embodiment employs a dichroic prism. This dichroic prism transmits light having a wavelength other than a wavelength band of 500 to 650 nm with respect to the light traveling from the image forming lens 37 toward the barrier filter part 94. Further, the dichroic prism reflects light having a wavelength in a range of 500 to 650 nm coming from a direction intersecting with the optical axis LC of the imaging optical system 30 to the dichroic prism, toward the objective lens 31. Specifically, the optical-path combining part 87 of the present embodiment reflects the light having the wavelength band of 500 to 650 nrn and transmits the light having the wavelength other than a wavelength band of 500 to 650 nm. A fixation target presenting part 86 is provided at a base end of the fixation target presenting optical system. This fixation target presenting part 86 of the present embodiment is an LCD (Liquid Crystal Display). The fixation target presenting part 86 has a presenting surface capable of lighting in a dot matrix pattern by the LCD. Back lights included in the LCD emit the light having the wavelength band of 500 to 650 nm from the fixation target presenting part 86. The light (presented image) emitted from the fixation target presenting part 86 is reflected by the optical-path combining part 87 and then projected to the fundus ER of the examinee's eye E through the image forming lens 37, the objective lens 31, and others.

The imaging optical system 30 of the present embodiment includes the optical-path combining part 87, the barrier filter part 94, the imaging device 95, and the fixation target presenting part 86 in a single module 260. The ophthalmic apparatus 100A of the first embodiment described above is arranged to move the focusing lens 36 in the axial direction of the optical axis LC of the imaging optical system 30 in order to perform focusing with the fundus ER of the examinee's eye E. On the other hand, the ophthalmic apparatus 100B of the second embodiment is arranged not to move the focusing lens 36 in the axial direction of the optical axis LC of the imaging optical system 30, but arranged to move the module 260 in the axial direction of the optical axis LC of the imaging optical system 30 by a drive unit 274 in order to perform focusing with the fundus ER of the examinee's eye E. Specifically, the fixation target presenting part 86 for presenting a fixation target to the examinee's eye E and the imaging device 95 for imaging the fundus ER of the examinee's eye E are fixedly placed in a single member constituting the single module 260. This module 260 is relatively displaced with respect to other parts or components of the imaging optical system 30 to perform focusing with the fundus ER of the examinee's eye E. A focusing method in the present embodiment can address a wide diopter scale (diopter value) of an examinee's eye E even if a moving distance of the module 260 is short as compared with the method of moving the focusing lens 36 in the first embodiment. Accordingly, the imaging optical system 30 (imaging part 3B) of the present embodiment can be reduced in size.

In the present embodiment, the imaging device 95 is shared between observation (infrared light) using the light source 52B and photographing (visible light) using the first light source 14. To be specific, the infrared light (a center wavelength of 850 nm) projected by the second light projecting optical system 20 mentioned later and reflected by the examinee's eye E is imaged by the imaging device 95 through the barrier filter part 94 (transmission of a 700 to 850 nm band). Further, fluorescence (autofluorescence) occurring in the examinee's eye E by the first light projecting optical system 10 mentioned later is imaged by the imaging device 95 through the barrier filter part 94 (transmission of a 700 to 850 nm band). Accordingly, observation and photographing of the fundus ER of the examinee's eye E are performed by the single imaging device 95. Thus, the imaging part 3B can be simplified and the low-cost ophthalmic apparatus 100B can be provided.

<2-3. First Light Projecting Optical System>

The first light projecting optical system 10 of the present embodiment is an optical system for projecting autofluorescence excitation light (blue-green) to the fundus ER of the examinee's eye E in order to obtain an autofluorescence fundus image of the examinee's eye E. The first light projecting optical system 10 of the present embodiment includes the objective lens 31, the fourth optical-path combining part 89, the first optical-path combining part 32B, the first light restricting part 12, the light restricting part 13, and the first light source 14. The first optical-path combining part 32B is a dichroic mirror and has the property of reflecting light with a center wavelength of 490 nm corresponding to the light emitted by the first light projecting optical system 10 and transmitting light having a center wavelength of 850 nm corresponding to the light emitted by the second light projecting optical system 20 and light having a wavelength band of 500 to 650 nm emitted by the fixation target presenting part 86. Thus, the first optical-path combining part 32B of the present embodiment has the property of reflecting the light having a center wavelength of 490 nm and transmitting the light having a wavelength band of 500 to 880 nm. It is to be noted that the light restricting part 13 is provided in the first image forming position conjugate with the pupil EP of the examinee's eye E. The first light restricting part 12 is provided between the light restricting part 13 and the first optical-path combining part 32B. In the present embodiment, the first light restricting part 12 is provided at a position conjugate with the back surface EL1 of the crystalline lens EL of the examinee's eye E. The first optical-path combining part 32B is provided between the objective lens 31 and the first image forming position conjugate with the pupil EP of the examinee's eye E. The light emitted from the first light source 14 passes through the opening of the light restricting part 13 and the opening of the first light restricting part 12 and then is reflected by the first optical-path combining part 32B toward the objective lens 31, passes through the fourth optical-path combining part 89 and the objective lens 31, and thus is projected to the examinee's eye E. It is to be noted that the first optical-path combining part 32B may have the function of the barrier filter part 94 of the present embodiment.

<2-4. Second Light Projecting Optical System>

Figure 8:
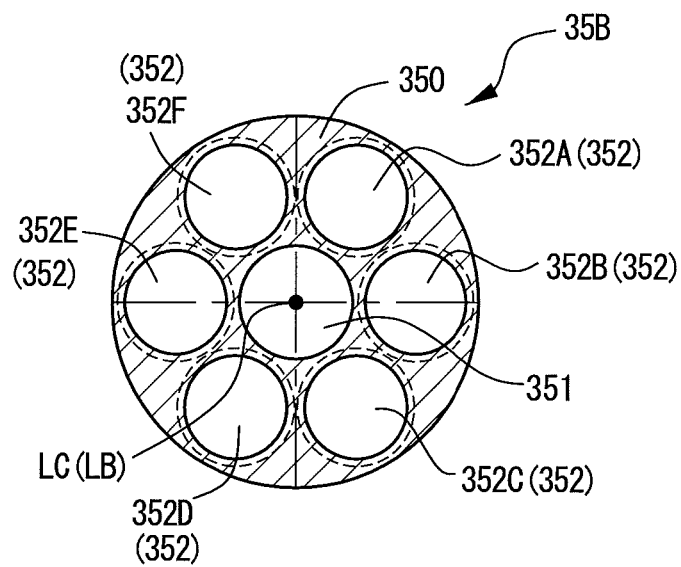
FIG. 8 is an explanatory view to explain an imaging diaphragm of the second embodiment.

The second light projecting optical system 20 of the present embodiment is an optical system for projecting infrared light (substantially colorless) to the fundus ER of the examinee's eye E in order to obtain an observation image of the fundus ER of the examinee's eye E. The second light projecting optical system 20 of the present embodiment includes the objective lens 31, the fourth optical-path combining part 89, the first optical-path combining part 32B, the imaging diaphragm 35B, and the light source 52B. The optical axis LB of the second light projecting optical system 20 is made coaxial with the optical axis LC of the imaging optical system 30. The light source 52B of the present embodiment employs a light source that emits infrared light. The light source of the light source 52B consists of a plurality of LEDs. Each of the LEDs is placed in a position apart from the optical axis (optical axis LB, optical axis LC). The light source 52B of the present embodiment is a light source that emits light with a center wavelength of 850 nm. The imaging diaphragm part 35B of the present embodiment is a plate-like member including a plate 350 formed with a first hole 351 and second holes 352 (see FIG. 8). The plate 350 is a support base. A center of the first hole 351 is coincident with the optical axis LC of the imaging optical system 30. The first hole 351 allows passage of the imaging light of the imaging optical system 30. The second holes 352 allow passage of the projection light of the second light projecting optical system 20. The second holes 352 in the present embodiment are a plurality of holes (352A to 352F), concretely, six holes corresponding to the number of LEDs constituting the light source 52B. The first hole 351 is provided at the center of the plate 350 and the second holes 352 are provided around the first hole 351. The first hole 351 and the second holes 352 are separately provided in the plate 350 to allow the light emitted from the light source 52B to pass through only the second holes 352. On the other hand, the imaging light of the imaging optical system 30 traveling in a direction from the objective lens 31 toward the imaging diaphragm part 35B reaches the imaging device 95 by passing through only the first hole 351.

For instance, in order to allow the projection light (the second light projecting optical system 20) and the imaging light (the imaging optical system 30) to appropriately individually pass through the imaging diaphragm part 35B, this imaging diaphragm part 35B may be formed with a barrier (a wall) extending in a direction of an optical axis (optical axis LB, optical axis LC). The imaging diaphragm part 35B of the present embodiment is provided at a position conjugate with the pupil EP of the examinee's eye E. The light (infrared light) emitted from the light source 52B passes through the second holes 352 (a light projection unit) of the imaging diaphragm part 35B and then passes through the first optical-path combining part 32B, the fourth optical-path combining part 89, and the objective lens 31 in this order to be projected to the examinee's eye E. The light emitted from the light source 52B and reflected by the examinee's eye E passes through the objective lens 31, the fourth optical-path combining part 89, the first optical-path combining part 32B, and the first hole 351 (an imaging unit) of the imaging diaphragm part 35B in this order and then is imaged by the imaging device 95 through the other optical parts or components of the imaging optical system 30. In the present embodiment, the imaging diaphragm part 35B is shared between the second light projecting optical system 20 and the imaging optical system 30, so that the projection light and the imaging light can be appropriately separated at the position conjugate with the pupil EP of the examinee's eye E even by a simple structure. Accordingly, an appropriate fundus image can be obtained with reduced unwanted reflection light.

<2-5. Anterior Segment Observation Optical System>

The anterior segment observation optical system 40 of the present embodiment will be explained below. The anterior segment observation optical system 40 of the present embodiment is an optical system for imaging the anterior segment of the examinee's eye E in order to allow observation of the anterior segment of the examinee's eye E. The anterior segment observation optical system 40 includes the objective lens 31, the fourth optical-path combining part 89, a mirror 45, the filed lens 41, the relay lens 42, and the imaging device 43. The fourth optical-path combining part 89 is a member for combining the optical path of the anterior segment observation optical system 40 and the optical path of the imaging optical system 30. That is, the fourth optical-path combining part 89 coaxially combines the optical axis LD and the optical axis LC. The fourth optical-path combining part 89 is provided between the objective lens 31 and the first optical-path combining part 32B. The fourth optical-path combining part 89 of the present embodiment is a dichroic mirror having the property of reflecting light having a 950-nm center wavelength corresponding to the wavelength of the light source of the alignment target part 250, and transmitting light having a 490-nm center wavelength corresponding to the light of the first light source 14, light having a wavelength band of 700 to 850 nm corresponding to the autofluorescence and the light of the light source 52B, and light having a wavelength band of 500 to 650 nm corresponding to the light emitted by the fixation target presenting part 86. Thus, the fourth optical-path combining part 89 of the present embodiment has the property of reflecting light having a center wavelength of 950 nm and transmitting light having a wavelength band of 490 to 850 nm. Accordingly, the light emitted from the light source of the alignment target part 250 is reflected by the anterior segment of the examinee's eye E, then passes through the objective lens 31, the fourth optical-path combining part 89, the mirror 45, the field lens 41, and the relay lens 42 in this order, and is imaged by the imaging device 43. Thus, the anterior segment image of the examinee's eye E illuminated with infrared light is obtained by the imaging device 43.

As explained above, the imaging part 3B of the ophthalmic apparatus 100B of the present embodiment includes an imaging unit for performing fundus observation, autofluorescence photographing, and anterior segment observation. The fundus observation is performed in such a way as to project light having a wavelength band with a 850-nm center wavelength by use of the second light projecting optical system 20 to the examinee's eye E, and obtain the fundus observation image by the light having a wavelength band with a 880-nm center wavelength by use of the imaging optical system 30. Furthermore, the autofluorescence photographing is performed in such a way as to project light with a center wavelength of 490 nm as the autofluorescence excitation light by use of the first light projecting optical system 10 to the examinee's eye E, and obtain the autofluorescence fundus image by the light having a wavelength band of 700 to 850 nm by use of the imaging optical system 30. The anterior segment observation is performed in such a way as to project light with a 950-nm center wavelength by use of the light source of the alignment target part 250 to the examinee's eye E, and obtain the anterior segment observation image of the examinee's eye E by the light with a 950-nm center wavelength by use of the anterior segment observation optical system 40.

<2-6. Removal of Unnecessary Light>

A method of removing unwanted light in the present embodiment will be explained below. In the ophthalmic apparatus 100B of the second embodiment, the first light source 14 is provided at the same conjugate position with the examinee's eye E as that in the ophthalmic apparatus 100A of the first embodiment. The conjugate positional relationship of the light restricting part 13, the first light restricting part 12, and the imaging diaphragm 35 (35A, 35B) is the same between the first embodiment and the second embodiment. Accordingly, as explained in the first embodiment, unwanted light arising in the examinee's eye E can be removed appropriately (see FIGS. 3A and 3B). Also in the present embodiment, the second light projecting optical system 20 projects the light to the examinee's eye E from a different direction from the optical path of the first light projecting optical system 10, and the imaging optical system 30 images the fundus ER of the examinee's eye E. Thus, the fundus ER of the examinee's eye E can be imaged with the optical property different from the first light projecting optical system 10. In the second embodiment, the unwanted light removing mechanism of the second light projecting optical system 20 is simplified, thus enabling achieving the more simplified imaging part 3B of the ophthalmic apparatus 100B. For instance, the imaging part 3B can be reduced in size and the ophthalmic apparatus 100B can be provided at low cost. In the second embodiment, the second light projecting optical system 20 and the imaging optical system 30 are used to observe the fundus ER of the examinee's eye E with infrared light, and the first light projecting optical system 10 and the imaging optical system 30 are used to fluorescently photograph the fundus ER of the examinee's eye E. Accordingly, the anterior segment image of the examinee's eye E can be observed through the anterior segment observation optical system 40 branching from the imaging optical system 30 at a different position from the first light projecting optical system 10. This makes it possible to appropriately perform alignment with the examinee's eye E and obtain a fluorescence image of the fundus ER of the examinee's eye E appropriately with reduced unwanted light even by a simple light source.

In the present embodiment, the property of the barrier filter part 94 is determined so as to transmit a wavelength band of 700 to 850 nm, but is not limited thereto. For instance, if it is controlled to turn off the light source of the alignment target part 250 (950-nm center wavelength) and the light source 52B (850-nm center wavelength) during imaging of autofluorescence, the property of the barrier filter part 94 may be set as the long pass filter property that transmits light at 700 nm or more. In the present embodiment, the first light source 14 employs the light source that lights up with a 490-nm center wavelength nm, but is not limited thereto. For instance, a light source that lights up with a 475-nm center wavelength may be used. Another alternative is to project the light having a wavelength band of 500 to 600 nm as autofluorescence excitation light by use of the light projecting optical system 10 and image the light having a wavelength band of 650 to 750 nm as autofluorescence by use of the imaging optical system 30.

<2-7. Use Method>

A use method of the ophthalmic apparatus 100B configured as above will be explained below. Firstly, the autofluorescence photographing is explained. Upon power-on, the controller 200 performs an initializing operation of for example a presenting positon of fixation targets, and others. The fixation-target presenting position can be changed when an examiner operates a predetermined visual-line direction changing switch provided in the switch part 230.

After completion of the initializing operation, the controller 200 turns on the light source of the alignment target part 250 to project infrared light to the anterior segment of the examinee's eye E. The controller 200 displays, on the monitor 8, the anterior segment observation image based on an output signal of the imaging device 43 imaging the anterior segment of the examinee's eye E. The examiner requests the examinee to put the examinee's head on the head support part 5. While observing the anterior segment observation image displayed on the monitor 8, the examiner operates the joystick 4 to move the imaging part 3 to right and left, and up and down to align the examinee's eye E and the imaging part 3. The examiner presses a changeover switch not shown provided in the switch part 230. Upon detecting that the changeover switch has been pressed, the controller 200 changes over the signal to be used for display on the monitor 8 from the output signal of the imaging device 43 to an output signal of the imaging device 83. In association with this control, the image displayed on the monitor 8 is changed from the anterior segment observation image based on the output signal of the imaging device 43 to the fundus observation image based on the output signal of the imaging device 83. Further, the controller 200 turns on the light source 52B.

The examiner observes a focusing degree of the fundus observation image (infrared observation image) displayed on the monitor 8 observation image and operates a predetermined focusing knob provided on the switch part 230 to perform focus adjustment. When detecting the operation of the switch part 230, the controller 200 drives the module 260 in the axial direction. When this focus adjustment is performed by the examiner, the fundus ER of the examinee's eye E and the imaging device 95 come into a conjugate positional relationship. Subsequently, the examiner presses the photographing switch 4b. When detecting the photographing switch 4b is pressed, the controller 200 outputs a photographing start signal. The controller 200 turns off the anterior segment observation illumination and the light source 52B. Successively, the controller 200 turns on the first light source 14 to project excitation light for autofluorescence to the fundus ER of the examinee's eye E. The autofluorescence occurring in the fundus ER is received by the imaging device 95 through the optical parts or components of the imaging optical system 30 such as the objective lens 31 and the barrier filter part 94. The controller 200 displays on the monitor 8 the autofluorescence fundus image based on the output signal of the imaging device 95. The controller 200 stores, in the storage unit 240, image data of the autofluorescence fundus image generated based on the output signal of the imaging device 95.

3. Operation and Advantage

In the ophthalmic apparatus 100 of the present disclosure, the imaging diaphragm part 35A for restricting the light from the fundus ER passing through the position conjugate with the pupil EP of the examinee's eye E is placed between the objective lens 31 and the imaging device 95. There is further provided with the imaging optical system 30 including the imaging device 95 for capturing the fundus image of the examinee's eye E through the objective lens 31 and the imaging diaphragm part 35A. The apparatus 100 further includes the first light projecting optical system 10 having the first light source 14 and being configured to project the light having a first wavelength ($\lambda$1) emitted from the first light source 14 and restricted or limited in range for passage through the pupil EP of the examinee's eye E, as the autofluorescence excitation light through the objective lens 31 to the examinee's eye E. Herein, the first optical-path combining part 32A is provided to allow the imaging optical system 30 and the first light projecting optical system 10 to share at least part of the optical path. The first optical-path combining part 32A is placed between the objective lens 31 of the imaging optical system 30 and the conjugate position with the pupil EP of the examinee's eye E. This configuration makes it possible to efficiently project the light of the first light source 14 to the fundus ER and obtain an appropriate fundus image with reduced influence of unwanted light (that is, fluorescence and reflection light from an unnecessary portion). As one example, even in photographing of autofluorescence needing a large amount of light, the light source can be simply configured. Further, the synergistic effect of the action that the light from the examinee's eye E is restricted or limited by the imaging diaphragm part 35A and the action that the light of the first light projecting optical system 10 is restricted or limited in passing through the pupil EP can appropriately suppress or reduce fluorescence and reflection light occurring from an unnecessary portion in the examinee's eye E.

The ophthalmic apparatus 100 of the present disclosure is provided with the second light projecting optical system 20 including the second light source 28 to project the light having a second wavelength (λ2) different from the first wavelength (λ1) by use of the light emitted from the second light source 28 to the fundus ER of the examinee's eye E. Herein, the second light projecting optical system 20 is configured to project the light of the second light source 28 to the fundus ER of the examinee's eye E via the shared optical path and the objective lens 31, the light having traveled from the different direction from the first light projecting optical system 10 and along the shared optical path at least part of which is shared between the imaging optical system 30 and the first light projecting optical system 10 by the first optical-path combining part 32A. With this configuration, the light having the second wavelength is projected to the examinee's eye E by use of the property of the light projecting optical system different from imaging using the first wavelength, so that the fundus image can be appropriately imaged. As one example, the use of the infrared light as the second wavelength enables prompt alignment with the examinee's eye E without giving any uncomfortable feeling to the examinee. Further, since the fundus ER of the examinee's eye E can be imaged by use of the light projecting optical system different in numerical aperture (NA), the light source can be simplified in structure and the apparatus can be provided at low cost.

The ophthalmic apparatus 100 of the present disclosure is provided with the second optical-path combining part 34 for allowing at least part of the optical path of the imaging optical system 30 and part of the optical path of the second light projecting optical system 20 to be shared, the second optical-path combining part 34 being provided at a position conjugate with the pupil EP of the examinee's eye E through the objective lens 31. Herein, the second light projecting optical system 20 is provided with the third light restricting part 21 placed between the second optical-path combining part 34 and the second light source 28 and configured to restrict the light emitted from the second light source 28 in transmitting the cornea EC of the examinee's eye E. With this configuration, even when the light having the second wavelength different from the first wavelength is projected by use of the different optical systems, the fundus image can be obtained with reduced unwanted fluorescence and reflection light arising in the examinee's eye E. As one example, even if a visible light having a wideband (e.g., 400 to 700 nm) for normal color fundus photographing is used as the second wavelength, it is possible to appropriately obtain a color fundus image apt to cause unwanted reflection light.

The ophthalmic apparatus 100 of the present disclosure is provided with the fourth light restricting part 27 placed between the third light restricting part 21 and the second light source 28 of the second light projecting optical system 20 and configured to restrict the light emitted from the second light source 28 from passing through the pupil EP of the examinee's eye E. With this configuration, the second light projecting optical system 20 projects the light from the second light source 28 to the fundus ER of the examinee's eye E through the light restricting part placed at each of the conjugate positions with the cornea EC and pupil EP of the examinee's eye E. Even if the light having the second wavelength different from the first wavelength is projected for photographing of autofluorescence, the fundus image can be obtained with reduced unwanted fluorescence and reflection light arising in the examinee's eye E. On the optical path generated between the third light restricting part 21 and the second light source 28 by placement of the second light source 28 at a position away from the objective lens 31 in terms of an optical path more than the fourth light restricting part 27, for example, the black-spot plate 23 for reducing unwanted reflection caused in the objective lens 31 can be placed. Thus, an appropriate fundus image with reduced unwanted light can be obtained.

The imaging optical system 30 of the ophthalmic apparatus 100 of the present disclosure is provided with the first optical-path combining part 32A between the objective lens 31 and the conjugate position with the crystalline-lens back surface EU of the examinee's eye E. The first light projecting optical system 10 is provided with the first light restricting part 12 placed between the first light source 14 and the first optical-path combining part 32A and configured to restrict the light emitted from the first light source 14. With this configuration, the light restricting part for restricting the light of the first light source 14 is easily placed on a side closer to the positon conjugate with the fundus ER than the position conjugate with the pupil EP in the first light projecting optical system 10. Accordingly, even a simple structure can efficiently project the light of the first light source 14 to the fundus ER of the examinee's eye E and also appropriately reduce unwanted fluorescence and reflection light arising in any portion other than the fundus of the examinee's eye E.

The imaging optical system 30 of the ophthalmic apparatus 100 of the present disclosure is configured to include the barrier filter part 94 between the imaging diaphragm part 35A and the imaging device 95, the barrier filter part 94 being configured to allow the imaging device 95 to image the autofluorescence generated in the fundus ER of the examinee's eye E by the first light projecting optical system 10. With this configuration, as one example, the first optical-path combining part 32A can be manufactured at low cost and thus the inexpensive ophthalmic apparatus 100 can be provided. Furthermore, the inexpensive ophthalmic apparatus can be achieved without needing a complicated structure between the objective lens 31 and the imaging diaphragm part 35A.

The first optical-path combining part 32A of the ophthalmic apparatus 100 of the present disclosure may be designed to have the optical property of a barrier filter so that the imaging device 95 images the autofluorescence occurring in the fundus ER of the examinee's eye E by the first light projecting optical system 10. With this configuration, for example, simply inserting of the first optical-path combining part 32A into the imaging optical system 30 enables obtaining an appropriate autofluorescence image as compared with a case where the first light projecting optical system 32A is arranged to be inserted in and removed from the imaging optical system 30. This makes it possible to provide the inexpensive ophthalmic apparatus without needing a complicated structure, and reduce the number of movable parts, resulting in an ophthalmic apparatus with little possibility of breakage.

The ophthalmic apparatus 100 of the present disclosure is provided with the third optical-path combining part 11 between the first optical-path combining part 32A and the first light source 14. Further, the light receiving unit provided in the optical path branching from the first light projecting optical system 10 by the third optical-path combining part 11 is configured to obtain an image of a portion different from the fundus ER of the examinee's eye E. Since the anterior segment image of the examinee's eye E is obtained with this configuration, for example, an alignment operation to obtain the fundus image is facilitated. Accordingly, an appropriate fluorescence fundus image can be obtained by use of the first light source 14 by a simple operation.

The ophthalmic apparatus 100 of the present disclosure is provided with the fourth optical-path combining part 89 between the objective lens 31 and the first optical-path combining part 32A. The light receiving unit provided in the optical path branching from the imaging optical system 30 by the fourth optical-path combining part 89 is configured to obtain an image of a portion different from the fundus ER of the examinee's eye E. Since the anterior segment image of the examinee's eye E is obtained with this configuration, for example, an alignment operation to obtain the fundus image is facilitated. Accordingly, an appropriate fluorescence fundus image can be obtained by use of the first light source 14 by a simple operation.

The ophthalmic apparatus 100 of the present disclosure is configured such that the first light source 14 is placed between the first light restricting part 12 and the position conjugate with the cornea EC of the examinee's eye E through the objective lens 31. This configuration can efficiently project the light of the first light source 14 to the fundus ER of the examinee's eye E. As one example, the light source can be simplified and an inexpensive ophthalmic apparatus can be provided.

In the present disclosure, it is arranged to image a portion (anterior segment) different from the fundus ER of the examinee's eye E by use of the anterior segment observation optical system 40, but not limited thereto. As an alternative, an optical system for obtaining a retinal tomographic image using an optical coherence technique may be employed instead of the anterior segment observation optical system 40. It may also be arranged to obtain a tomographic image of the anterior segment. In this case, it is also possible to appropriately change the property of the optical-path combining member such as the third optical-path combining part 11 and the first optical-path combining part 32 to match the wavelengths of the light source used in this optical coherence. This configuration can provide an ophthalmic apparatus capable of appropriately obtaining a fundus image including a tomographic image even by a simple structure. As another alternative, an apparatus may also be designed to include only the imaging part 3 of the present disclosure, that is, designed as a hand-held ophthalmic apparatus. Since the optical systems of the present disclosure efficiently guide the light emitted from the light source to the fundus ER of the examinee's eye E, the hand-held ophthalmic apparatus capable of appropriately obtaining a fundus image even by a simple structure can be provided.

In the present disclosure, the first light projecting optical system 10 is configured to project excitation light used for autofluorescence photographing. The first light projecting optical system 10 may also be configured to project light other than the autofluorescence excitation light. For example, it may be used to project excitation light for FAG fluorescence photographing or to project excitation light for ICG fluorescence photographing. The first light projecting optical system 10 may also be used for projecting light having a specific wavelength for filter photographing such as red-free photographing or used for projecting illumination light having a wavelength band of 400 to 700 nm for normal color photographing. Further, two or more different types of light sources may be arranged in a place of the first light source 14 to selectively emit light having one of a plurality of wavelengths from the place of the first light source 14. For instance, LEDs different in wavelength may be arranged alternately. The first light restricting part 12 and the light restricting part 13 of the present disclosure may have a spectral characteristic at an opening portion for restricting a light beam. Since the light restricting part has the spectral characteristic, it is possible to change a light restricting region according to the emission wavelength of the first light source 14. For example, some regions having different spectral transmittances are preferably formed by etching treatment. This configuration can change the diameter of the light beam to be projected according to the wavelength to be projected without inserting/removing the light restricting part or without changing the opening diameter of the light restricting part such as the first light restricting part 12 and the light restricting part 13. Accordingly, an ophthalmic apparatus capable of obtaining an appropriate fundus image even by a simple structure can be provided.

In the present disclosure, the excitation light for autofluorescence is projected from the first light projecting optical system 10 and the infrared light or normal color photographing light is projected from the second light projecting optical system 20. As an alternative, excitation light for FAG fluorescence photographing or ICG fluorescence photographing may be projected from the second light projecting optical system 20. The use of the light projecting optical system under the different projecting method can provide an ophthalmic apparatus capable of obtaining an appropriate fundus image even by a simple structure. For instance, the light projecting optical system of autofluorescence needing a large amount of light is the first light projecting optical system 10 of the present disclosure, so that the light source of the ophthalmic apparatus can be achieved as a simple structure.

The embodiments disclosed above are mere examples, but not restrictive, and the present disclosure is not limited to the above explanations and is intended to cover various modifications and variations within the scope of the appended claims.

What is claimed is:

1. An ophthalmic apparatus comprising:
   an imaging optical system including an imaging diaphragm placed between an objective lens and an imaging device to restrict light from a fundus, the light having passed through a position conjugate with a pupil of an examinee's eye, the imaging optical system being configured to image a fundus image of the examinee's eye by use of the imaging device through the objective lens and the imaging diaphragm;
   a first light projecting optical system including a first light source to emit light having a first wavelength and being configured to project the light with the first wavelength, emitted from the first light source and restricted in range for passage through the pupil of the examinee's eye, as autofluorescence-inducing excitation light to the examinee's eye through the objective lens; and
   a first optical-path combining member configured to allow the imaging optical system and the first light projecting optical system to share at least part of an optical path with each other,
   wherein the first optical-path combining member is provided between the objective lens and a conjugate position to be conjugated with the pupil of the examinee's eye through the objective lens in the imaging optical system.

2. The ophthalmic apparatus according to claim 1, further comprising a second light projecting optical system including a second light source to emit light having a second wavelength different from the first wavelength and being configured to project the light with the second wavelength to the fundus of the examinee's eye, wherein the second light projecting optical system projects the light emitted from the second light source to the fundus of the examinee's eye through the shared optical path and the objective lens from a different projection direction from a projection direction of the first light projecting optical system by directing the light from the second light source toward the shared optical path of the imaging optical system and the first light projecting optical system by the first optical-path combining member.

3. The ophthalmic apparatus according to claim 2, further comprising a second optical-path combining member provided at a position conjugate with a pupil of the examinee's eye through the objective lens and configured to allow the imaging optical system and the second light projecting optical system to share at least part of an optical path with each other, wherein the second light projecting optical system is provided with a third light restricting member placed between the second optical-path combining member and the second light source and configured so that the light emitted from the second light source is restricted in range for passage through a cornea of the examinee's eye.

4. The ophthalmic apparatus according to claim 3, wherein the second light projecting optical system is further provided with a fourth light restricting member placed between the third light restricting member and the second light source and configured so that the light emitted from the second light source is restricted in range for passage through a pupil of the examinee's eye.

5. The ophthalmic apparatus according to claim 1, wherein the first optical-path combining member is provided between the objective lens and a conjugate position in the imaging optical system with a rear surface of a crystalline lens of the examinee's eye through the objective lens, and the first light projecting optical system is further provided with a first light restricting member placed between the first light source and the first optical-path combining member and configured so that the light emitted from the first light source is restricted from widening.

6. The ophthalmic apparatus according to claim 5, wherein the first light source is placed between the first light restricting member and a position to be conjugated with a cornea of the examinee's eye through the objective lens.

7. The ophthalmic apparatus according to claim 1, wherein the imaging optical system is provided with a barrier filter part between the imaging diaphragm part and the imaging device to allow the imaging device to image autofluorescence generated in the fundus of the examinee's eye by the first light projecting optical system.

8. The ophthalmic apparatus according to claim 1, wherein the first optical-path combining member has an optical property of functioning as a barrier filter to allow the imaging device to image autofluorescence generated in the fundus of the examinee's eye by the first light projecting optical system.

9. The ophthalmic apparatus according to claim 1, further comprising a third optical-path combining part between the first optical-path combining member and the first light source, so that the third optical-path combining part allows a light receiving part provided in an optical path branching from the first light projecting optical system to obtain an image of a portion different from the fundus of the examinee's eye.

10. The ophthalmic apparatus according to claim 1, further comprising a fourth optical-path combining part between the objective lens and the first optical-path combining member, so that the fourth optical-path combining part allows a light receiving part provided in an optical path branching from the first light projecting optical system to obtain an image of a portion different from the fundus of the examinee's eye.

* * * * *